United States Patent
To et al.

(10) Patent No.: US 11,224,522 B2
(45) Date of Patent: Jan. 18, 2022

(54) SURGICAL IMPLANT AND RELATED METHODS

(71) Applicant: INTEGRITY IMPLANTS INC., Palm Beach Gardens, FL (US)

(72) Inventors: John To, Newark, CA (US); Christopher Walsh, Palm Beach Gardens, FL (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 71 days.

(21) Appl. No.: 16/633,523

(22) PCT Filed: Jul. 24, 2018

(86) PCT No.: PCT/US2018/043517
§ 371 (c)(1),
(2) Date: Jan. 23, 2020

(87) PCT Pub. No.: WO2019/023251
PCT Pub. Date: Jan. 31, 2019

(65) Prior Publication Data
US 2020/0229939 A1    Jul. 23, 2020

Related U.S. Application Data

(60) Provisional application No. 62/536,335, filed on Jul. 24, 2017.

(51) Int. Cl.
*A61F 2/44*    (2006.01)
*A61F 2/30*    (2006.01)
*A61F 2/46*    (2006.01)

(52) U.S. Cl.
CPC .... *A61F 2/447* (2013.01); *A61F 2002/30014* (2013.01); *A61F 2002/30019* (2013.01);
(Continued)

(58) Field of Classification Search
CPC .......... A61F 2/44; A61F 2/442; A61F 2/4455; A61F 2/447; A61F 2002/30014;
(Continued)

(56) References Cited

U.S. PATENT DOCUMENTS 4,309,777 A    1/1982  Patil
4,733,665 A    3/1988  Palmaz
(Continued)

FOREIGN PATENT DOCUMENTS

CN    101909548    7/2014
EP    1011503    2/1998
(Continued)

OTHER PUBLICATIONS

U.S. Appl. No. 17/085,788, filed Sep. 21, 2016, To—owned by Applicant.
(Continued)

*Primary Examiner* — Eric S Gibson
(74) *Attorney, Agent, or Firm* — Brian S. Boyer; Syndicated Law, PC.

(57) ABSTRACT

The present disclosure describes an intervertebral implant having a laterovertically-expanding shell operable for a reversible expansion from a collapsed state into an expanded state, the laterovertically-expanding shell having a guide element, one or more connectors, and a pair of lateral extension elements that function to laterally expand the footprint of the implant within an intervertebal disc space.

20 Claims, 9 Drawing Sheets

(52) U.S. Cl.
CPC ............... *A61F 2002/3055* (2013.01); *A61F 2002/30131* (2013.01); *A61F 2002/30136* (2013.01); *A61F 2002/30177* (2013.01); *A61F 2002/30261* (2013.01); *A61F 2002/30331* (2013.01); *A61F 2002/30515* (2013.01); *A61F 2002/30904* (2013.01); *A61F 2002/30971* (2013.01); *A61F 2002/4629* (2013.01)

(58) Field of Classification Search
CPC .. A61F 2002/30019; A61F 2002/30331; A61F 2002/30515; A61F 2002/30565; A61F 2002/30733; A61F 2002/30971
See application file for complete search history.

(56) References Cited

U.S. PATENT DOCUMENTS

| | | |
|---|---|---|
| 4,759,766 A | 7/1988 | Buettner-Janz et al. |
| 4,820,305 A | 4/1989 | Harms et al. |
| 4,997,432 A | 3/1991 | Keller |
| 5,192,327 A | 3/1993 | Brantigan |
| 5,221,261 A | 6/1993 | Termin et al. |
| 5,609,635 A | 3/1997 | Michelson |
| 5,658,336 A | 8/1997 | Pisharodi |
| 5,976,187 A | 11/1999 | Richelsoph |
| 5,980,522 A | 11/1999 | Koros |
| 5,980,552 A | 11/1999 | Pinchasik et al. |
| 6,039,761 A | 3/2000 | Li et al. |
| 6,102,950 A | 8/2000 | Vaccaro |
| 6,126,689 A | 10/2000 | Brett |
| 6,176,882 B1 | 1/2001 | Biedermann |
| 6,193,757 B1 | 2/2001 | Foley et al. |
| 6,368,351 B1 | 4/2002 | Glenn et al. |
| 6,375,682 B1 | 4/2002 | Fleischmann et al. |
| 6,395,031 B1 | 5/2002 | Foley et al. |
| 6,409,766 B1 | 6/2002 | Brett |
| 6,419,705 B1 | 7/2002 | Erickson |
| 6,425,919 B1 | 7/2002 | Lambrecht et al. |
| 6,432,107 B1 | 8/2002 | Ferree |
| 6,436,119 B1 | 8/2002 | Erb et al. |
| 6,443,989 B1 | 9/2002 | Jackson |
| 6,482,235 B1 | 11/2002 | Lambrecht et al. |
| 6,488,710 B2 | 12/2002 | Besselink |
| 6,491,724 B1 | 12/2002 | Ferree |
| 6,575,899 B1 | 6/2003 | Foley et al. |
| 6,582,439 B1 | 6/2003 | Sproul |
| 6,582,441 B1 | 6/2003 | He et al. |
| 6,582,467 B1 | 6/2003 | Teitelbaum |
| 6,595,998 B2 | 7/2003 | Johnson et al. |
| 6,666,891 B2 | 12/2003 | Boehm, Jr. et al. |
| 6,821,276 B2 | 11/2004 | Lambrecht et al. |
| 6,821,298 B1 | 11/2004 | Jackson |
| 6,893,464 B2 | 5/2005 | Kiester |
| 7,018,415 B1 | 3/2006 | McKay |
| 7,083,650 B2 | 8/2006 | Moskowitz et al. |
| 7,087,055 B2 | 8/2006 | Lim et al. |
| 7,204,853 B2 | 4/2007 | Gordon et al. |
| 7,214,243 B2 | 5/2007 | Taylor |
| 7,217,293 B2 * | 5/2007 | Branch, Jr. ............ A61F 2/447 623/17.16 |
| 7,316,686 B2 | 1/2008 | Dorchak et al. |
| 7,544,208 B1 | 6/2009 | Mueller et al. |
| 7,621,950 B1 | 11/2009 | Globerman et al. |
| 7,643,884 B2 | 1/2010 | Pond et al. |
| 7,655,046 B2 | 2/2010 | Dryer et al. |
| 7,678,148 B2 | 3/2010 | Peterman |
| 7,731,751 B2 | 6/2010 | Butler et al. |
| 7,771,473 B2 | 8/2010 | Thramann |
| 7,819,921 B2 | 10/2010 | Grotz |
| 7,828,845 B2 | 11/2010 | Estes et al. |
| 7,828,849 B2 | 11/2010 | Lim |
| 7,846,206 B2 | 12/2010 | Oglaza et al. |
| 7,850,733 B2 | 12/2010 | Baynham et al. |
| 7,862,618 B2 | 1/2011 | White et al. |
| 7,879,098 B1 | 2/2011 | Simmons, Jr. |
| 7,909,872 B2 | 3/2011 | Zipnick |
| 7,918,888 B2 | 5/2011 | Hamada |
| 7,951,202 B2 | 5/2011 | Ralph et al. |
| 8,062,375 B2 | 11/2011 | Glerum et al. |
| 8,070,754 B2 | 12/2011 | Fabian et al. |
| 8,070,813 B2 | 12/2011 | Grotz et al. |
| 8,083,744 B2 | 12/2011 | Dorchak |
| 8,088,163 B1 | 1/2012 | Kleiner |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,123,810 B2 | 2/2012 | Gordon et al. |
| 8,167,950 B2 | 5/2012 | Aferzon et al. |
| 8,182,538 B2 | 5/2012 | O'Neil et al. |
| 8,187,332 B2 | 5/2012 | McLuen |
| 8,236,058 B2 | 8/2012 | Fabian et al. |
| 8,241,363 B2 | 8/2012 | Sommerich et al. |
| 8,267,939 B2 | 9/2012 | Cipoletti et al. |
| 8,273,129 B2 | 9/2012 | Baynham et al. |
| 8,353,961 B2 | 1/2013 | McClintock |
| 8,353,963 B2 | 1/2013 | Glerum |
| 8,398,713 B2 | 3/2013 | Weiman |
| 8,435,298 B2 | 5/2013 | Weiman |
| 8,491,659 B2 | 7/2013 | Weiman et al. |
| 8,518,120 B2 | 8/2013 | Glerum et al. |
| 8,523,944 B2 | 9/2013 | Jimenez et al. |
| 8,551,173 B2 | 10/2013 | Lechmann et al. |
| 8,556,979 B2 | 10/2013 | Glerum et al. |
| 8,628,578 B2 | 1/2014 | Miller et al. |
| 8,632,595 B2 | 1/2014 | Weiman |
| 8,663,332 B1 | 3/2014 | To |
| 8,685,098 B2 | 4/2014 | Glerum et al. |
| 8,845,731 B2 | 9/2014 | Weiman |
| 8,852,279 B2 | 10/2014 | Weiman et al. |
| 8,882,840 B2 | 11/2014 | Mcclintock et al. |
| 8,894,712 B2 | 11/2014 | Varela |
| 8,900,307 B2 | 12/2014 | Hawkins et al. |
| 8,926,704 B2 | 1/2015 | Glerum et al. |
| 8,936,641 B2 * | 1/2015 | Cain ...................... A61F 2/447 623/17.16 |
| 8,940,048 B2 | 1/2015 | Butler et al. |
| 8,940,052 B2 | 1/2015 | Lechmann et al. |
| 8,986,387 B1 | 3/2015 | To |
| 9,034,041 B2 | 5/2015 | Wolters |
| 9,039,771 B2 | 5/2015 | Glerum et al. |
| 9,044,342 B2 | 6/2015 | Perloff et al. |
| 9,060,876 B1 | 6/2015 | To |
| 9,066,813 B2 | 6/2015 | Farris et al. |
| 9,138,328 B2 | 9/2015 | Butler et al. |
| 9,155,628 B2 | 10/2015 | Glerum et al. |
| 9,186,259 B2 | 11/2015 | To |
| 9,216,095 B2 | 12/2015 | Glerum et al. |
| 9,241,806 B2 | 1/2016 | Suh |
| 9,278,008 B2 | 3/2016 | Perloff et al. |
| 9,295,562 B2 * | 3/2016 | Lechmann ............ A61F 2/4425 |
| 9,320,610 B2 | 4/2016 | Alheidt et al. |
| 9,333,092 B2 | 5/2016 | To |
| 9,351,848 B2 | 5/2016 | Glerum et al. |
| 9,402,733 B1 | 8/2016 | To |
| 9,402,739 B2 | 8/2016 | Weiman et al. |
| 9,421,110 B2 | 8/2016 | Masson |
| 9,439,782 B2 | 9/2016 | Kleiner |
| 9,445,918 B1 | 9/2016 | Lin et al. |
| 9,463,052 B2 | 10/2016 | Geist |
| 9,474,625 B2 | 10/2016 | Weiman |
| 9,480,574 B2 | 11/2016 | Lee et al. |
| 9,480,576 B2 | 11/2016 | Pepper et al. |
| 9,545,316 B2 | 1/2017 | Ashley et al. |
| 9,561,116 B2 | 2/2017 | Weiman et al. |
| 9,561,117 B2 * | 2/2017 | Lechmann ............ A61F 2/447 |
| 9,566,168 B2 | 2/2017 | Glerum et al. |
| 9,597,200 B2 | 3/2017 | Glerum et al. |
| 9,636,154 B2 | 5/2017 | Overes et al. |
| 9,655,744 B1 | 5/2017 | Pimenta |
| 9,675,466 B2 | 6/2017 | Overes et al. |
| 9,675,469 B2 | 6/2017 | Landry et al. |
| 9,717,601 B2 | 8/2017 | Miller |
| 9,730,803 B2 | 8/2017 | DiMauro et al. |
| 9,737,411 B2 | 8/2017 | Loebl et al. |

(56) References Cited

U.S. PATENT DOCUMENTS

| | | |
|---|---|---|
| 9,795,493 B1 | 10/2017 | Bannigan |
| 9,801,640 B2 | 10/2017 | O'Neil et al. |
| 9,801,733 B2 | 10/2017 | Wolters et al. |
| 9,801,734 B1 | 10/2017 | Stein et al. |
| 9,883,953 B1 | 2/2018 | To |
| 9,889,019 B2 | 2/2018 | Rogers et al. |
| 9,907,673 B2 | 3/2018 | Weiman et al. |
| 9,913,727 B2 * | 3/2018 | Thommen ............ A61F 2/4425 |
| 9,913,736 B2 | 3/2018 | To |
| 9,987,143 B2 | 6/2018 | Robinson et al. |
| 9,999,517 B2 | 6/2018 | To |
| 10,052,215 B2 | 8/2018 | Hessler et al. |
| 10,058,350 B2 | 8/2018 | Geist |
| 10,080,592 B2 | 9/2018 | Geist |
| 10,085,849 B2 | 10/2018 | Weiman et al. |
| 10,098,757 B2 | 10/2018 | Logan et al. |
| 10,105,238 B2 * | 10/2018 | Koch ..................... A61F 2/44 |
| 10,137,007 B2 | 11/2018 | Dewey et al. |
| 10,143,565 B2 | 12/2018 | Farris et al. |
| 10,143,569 B2 | 12/2018 | Weiman et al. |
| 10,149,773 B2 | 12/2018 | To |
| 10,154,911 B2 | 12/2018 | Predick et al. |
| 10,226,356 B2 | 3/2019 | Grotz |
| 10,226,360 B2 | 3/2019 | Baynham |
| 10,238,503 B2 | 3/2019 | Kuyler et al. |
| 10,251,759 B2 | 4/2019 | Butler et al. |
| 10,265,192 B2 | 4/2019 | Eastlack et al. |
| 10,322,009 B2 * | 6/2019 | Aghayev ............... A61F 2/447 |
| 10,322,014 B2 | 6/2019 | To |
| 10,342,675 B2 | 7/2019 | Alheidt |
| 10,383,743 B2 | 8/2019 | To |
| 10,413,419 B2 | 9/2019 | Thibodeau |
| 10,426,634 B1 | 10/2019 | Al-Jazaeri et al. |
| 10,441,430 B2 | 10/2019 | Ludwig et al. |
| 10,470,891 B2 | 11/2019 | Sharifi-Mehr et al. |
| 10,470,894 B2 | 11/2019 | Foley et al. |
| 10,485,675 B2 | 11/2019 | Sharifi-Mehr et al. |
| 10,492,918 B2 | 12/2019 | DiMauro |
| 10,507,116 B2 * | 12/2019 | Shoshtaev ............. A61F 2/4611 |
| 10,531,964 B2 | 1/2020 | Miller et al. |
| 10,624,756 B2 | 4/2020 | Bernard et al. |
| 10,631,996 B2 | 4/2020 | Bernard et al. |
| 10,687,876 B2 | 6/2020 | Vrionis et al. |
| 10,709,578 B2 * | 7/2020 | Geist ................. A61B 17/7061 |
| 10,758,368 B2 * | 9/2020 | To ........................ A61F 2/442 |
| 10,786,366 B2 * | 9/2020 | To ........................ A61F 2/447 |
| 10,898,340 B2 * | 1/2021 | Koch ..................... A61F 2/4455 |
| 10,912,653 B2 * | 2/2021 | To ........................ A61F 2/4455 |
| 2002/0035400 A1 | 3/2002 | Bryan et al. |
| 2002/0040243 A1 | 4/2002 | Attali |
| 2003/0074075 A1 | 4/2003 | Thomas et al. |
| 2003/0083746 A1 | 5/2003 | Kuslich |
| 2004/0010315 A1 | 1/2004 | Song |
| 2004/0024463 A1 | 2/2004 | Thomas et al. |
| 2005/0113916 A1 * | 5/2005 | Branch, Jr. ............ A61F 2/447 623/17.11 |
| 2005/0256576 A1 | 11/2005 | Moskowitz et al. |
| 2006/0100706 A1 | 5/2006 | Shadduck |
| 2006/0122701 A1 | 6/2006 | Kiester |
| 2006/0167547 A1 | 7/2006 | Suddaby |
| 2006/0287729 A1 | 12/2006 | Segal et al. |
| 2007/0118222 A1 | 5/2007 | Lang |
| 2007/0173939 A1 | 7/2007 | Kim et al. |
| 2007/0219634 A1 | 9/2007 | Greenhalgh |
| 2008/0009876 A1 | 1/2008 | Sankaran et al. |
| 2008/0021556 A1 | 1/2008 | Edie |
| 2008/0021559 A1 | 1/2008 | Thramann |
| 2008/0147193 A1 | 6/2008 | Matthis |
| 2008/0234687 A1 | 9/2008 | Schaller |
| 2008/0281346 A1 | 11/2008 | Greenhalgh |
| 2008/0281424 A1 | 11/2008 | Parry et al. |
| 2009/0018524 A1 | 1/2009 | Greenhalgh |
| 2009/0076607 A1 | 3/2009 | Aalsma et al. |
| 2009/0138083 A1 | 5/2009 | Biyani |
| 2009/0281551 A1 | 5/2009 | Frey |
| 2009/0222043 A1 | 9/2009 | Altarac |
| 2009/0234389 A1 | 9/2009 | Chuang |
| 2010/0010542 A1 | 1/2010 | Jackson |
| 2010/0010633 A1 | 1/2010 | Kohm |
| 2010/0042218 A1 | 2/2010 | Nebosky et al. |
| 2010/0082109 A1 * | 4/2010 | Greenhalgh ............ A61F 2/447 623/17.15 |
| 2010/0198352 A1 | 8/2010 | Edie |
| 2010/0217325 A1 | 8/2010 | Hochschuler |
| 2010/0222884 A1 | 9/2010 | Greenhalgh |
| 2010/0234956 A1 | 9/2010 | Attia |
| 2010/0286783 A1 | 11/2010 | Lechmann et al. |
| 2010/0292796 A1 | 11/2010 | Greenhalgh |
| 2011/0022090 A1 | 1/2011 | Gordon |
| 2011/0029082 A1 | 2/2011 | Hall |
| 2011/0035011 A1 * | 2/2011 | Cain ..................... A61F 2/4611 623/17.16 |
| 2011/0046748 A1 | 2/2011 | Martin |
| 2011/0130835 A1 | 6/2011 | Ashley |
| 2011/0172774 A1 | 7/2011 | Varela |
| 2011/0190816 A1 | 8/2011 | Sheffer |
| 2011/0282453 A1 | 11/2011 | Greenhalgh |
| 2011/0301712 A1 | 12/2011 | Palmatier |
| 2011/0319997 A1 | 12/2011 | Glerum |
| 2012/0029636 A1 | 2/2012 | Ragab |
| 2012/0029645 A1 | 2/2012 | Fabian et al. |
| 2012/0035729 A1 | 2/2012 | Glerum et al. |
| 2012/0046748 A1 | 2/2012 | Weiman |
| 2012/0083889 A1 | 4/2012 | Purcell |
| 2012/0089185 A1 | 4/2012 | Gabelberger |
| 2012/0109319 A1 | 5/2012 | Perisic |
| 2014/0039625 A1 | 7/2012 | To |
| 2012/0209386 A1 | 8/2012 | Triplett et al. |
| 2012/0271396 A1 | 10/2012 | Zheng |
| 2012/0290090 A1 | 11/2012 | Glerum et al. |
| 2012/0303126 A1 | 11/2012 | Kirschman |
| 2013/0023996 A1 | 1/2013 | McCormack |
| 2013/0041471 A1 * | 2/2013 | Siegal ..................... A61F 2/442 623/17.16 |
| 2013/0184822 A1 | 7/2013 | Kleiner |
| 2014/0243981 A1 | 8/2014 | Davenport et al. |
| 2015/0100128 A1 | 4/2015 | Glerum et al. |
| 2015/0148908 A1 | 5/2015 | Marino et al. |
| 2015/0190242 A1 | 7/2015 | Blain et al. |
| 2015/0223946 A1 * | 8/2015 | Weiman ................. A61F 2/442 623/17.15 |
| 2015/0374508 A1 | 12/2015 | Sandul |
| 2016/0015530 A1 | 1/2016 | To |
| 2016/0038305 A1 * | 2/2016 | Weiman ................. A61F 2/442 623/17.16 |
| 2016/0256291 A1 | 9/2016 | Miller |
| 2016/0317315 A1 | 11/2016 | Weiman |
| 2016/0338854 A1 | 11/2016 | Serhan et al. |
| 2017/0056200 A1 * | 3/2017 | Koch ..................... A61F 2/4455 |
| 2017/0119540 A1 | 5/2017 | Greenhalgh |
| 2017/0172758 A1 * | 6/2017 | Field .................... A61F 2/4611 |
| 2017/0209282 A1 * | 7/2017 | Aghayev ............... A61F 2/447 |
| 2017/0224504 A1 | 8/2017 | Butler et al. |
| 2017/0224505 A1 | 8/2017 | Butler et al. |
| 2017/0231780 A1 | 8/2017 | D'urso |
| 2017/0239063 A1 | 8/2017 | Predick |
| 2017/0281358 A1 | 10/2017 | Wagner et al. |
| 2017/0333198 A1 | 11/2017 | Robinson |
| 2017/0333203 A1 | 11/2017 | Glerum |
| 2017/0354512 A1 | 12/2017 | Weiman et al. |
| 2018/0042735 A1 | 2/2018 | Schell et al. |
| 2018/0214221 A1 | 3/2018 | Crawford et al. |
| 2018/0185163 A1 | 7/2018 | Weiman et al. |
| 2018/0193164 A1 | 7/2018 | Shoshtaev |
| 2018/0256357 A1 | 9/2018 | To |
| 2018/0296361 A1 | 10/2018 | Butler et al. |
| 2018/0303626 A1 | 10/2018 | Rogers et al. |
| 2018/0344476 A1 * | 12/2018 | Koch ..................... A61F 2/44 |
| 2018/0360489 A1 | 12/2018 | Geist |
| 2018/0360617 A1 | 12/2018 | Fabian et al. |
| 2019/0053913 A1 | 2/2019 | To |
| 2019/0060085 A1 * | 2/2019 | Geist ................. A61B 17/8805 |
| 2019/0076263 A1 | 3/2019 | Emstad |
| 2019/0091033 A1 | 3/2019 | Dewey et al. |

(56) References Cited

U.S. PATENT DOCUMENTS

| | | | |
|---|---|---|---|
| 2019/0099278 | A1 | 4/2019 | Farris et al. |
| 2019/0110900 | A1 | 4/2019 | Suddaby |
| 2019/0110902 | A1 | 4/2019 | Vigliotti et al. |
| 2019/0117409 | A1 | 4/2019 | Shoshtaev |
| 2019/0117827 | A1 | 4/2019 | Casabonne et al. |
| 2019/0201209 | A1 | 7/2019 | Branch et al. |
| 2019/0209339 | A1 | 7/2019 | To |
| 2019/0240039 | A1 | 8/2019 | Walker et al. |
| 2019/0254836 | A1 | 8/2019 | Cowan et al. |
| 2019/0254841 | A1 | 8/2019 | To |
| 2019/0269521 | A1 | 9/2019 | Shoshtaev |
| 2019/0290448 | A1 | 9/2019 | Predick et al. |
| 2019/0307573 | A1 | 10/2019 | Sicotte et al. |
| 2019/0328544 | A1 | 10/2019 | Ashley et al. |
| 2019/0336299 | A1 | 11/2019 | Bernard et al. |
| 2020/0000607 | A1 | 1/2020 | To |
| 2020/0015985 | A1 | 1/2020 | Rogers et al. |
| 2020/0030110 | A1 | 1/2020 | Sharabani et al. |
| 2020/0046515 | A1 | 2/2020 | To |
| 2020/0093609 | A1 | 3/2020 | Shoshtaev |
| 2020/0113706 | A1 | 4/2020 | Robinson |
| 2020/0129307 | A1* | 4/2020 | Hunziker ............... A61F 2/4455 |
| 2020/0229939 | A1* | 7/2020 | To ......................... A61F 2/4455 |
| 2020/0352732 | A1 | 11/2020 | To |

FOREIGN PATENT DOCUMENTS

| | | |
|---|---|---|
| EP | 1233732 | 2/2001 |
| EP | 2327377 | 3/2002 |
| EP | 1532949 | 11/2003 |
| EP | 2237748 | 1/2009 |
| WO | WO 1996/040015 | 6/1996 |
| WO | WO 2000/044319 | 1/2000 |
| WO | WO 2001/066047 | 7/2001 |
| WO | WO 2005/112834 | 12/2005 |
| WO | WO 2008/005627 | 5/2007 |
| WO | WO 2007/076374 | 7/2007 |
| WO | WO 2008/035849 | 7/2007 |
| WO | WO 2008/033457 | 3/2008 |
| WO | WO 2008/089252 | 7/2008 |
| WO | WO 2008/121162 | 10/2008 |
| WO | WO 2010/077359 | 7/2010 |
| WO | WO 2012/135764 | 10/2012 |
| WO | WO 2014/164625 | 10/2014 |
| WO | WO 2016/019241 | 2/2016 |
| WO | WO 2017/004503 | 1/2017 |

OTHER PUBLICATIONS

U.S. Appl. No. 60/666,945 (priority for U.S. Pat. No. 7,731,751, cited herein), filed Mar. 31, 2005, Butler, et al.
U.S. Appl. No. 61/585,724 (priority for U.S. Pat. No. 9,463,052, cited herein), filed Jan. 12, 2012, Geist—owned by Applicant.
U.S. Appl. No. 61/737,054, filed Dec. 15, 2013, To—owned by Applicant.
U.S. Appl. No. 61/875,688, filed Oct. 4, 2013, To—owned by Applicant.
U.S. Appl. No. 62/232,021 (priority for U.S. Pat. No. 10,058,350, cited herein), filed Sep. 24, 2015, Geist—owned by Applicant.
U.S. Appl. No. 62/444,663 (priority for U.S. 2018/0193164, cited herein), filed Jan. 10, 2017, Shoshtaev—owned by Applicant.
U.S. Appl. No. 62/471,206 (priority for U.S. 2018/0193164, cited herein), filed Jan. 10, 2017, Shoshtaev—owned by Applicant.
U.S. Appl. No. 62/481,565 (priority for U.S. 2018/0193164, cited herein), filed Jan. 10, 2017, Shoshtaev—owned by Applicant.
U.S. Appl. No. 62/536,335 (priority for PCT/US2018/43517, cited herein), filed Jul. 24, 2017, To—owned by Applicant.
U.S. Appl. No. 62/550,557 (priority for U.S. Appl. No. 16/113,040, cited herein), filed Aug. 25, 2017, Geist—owned by Applicant.
PCT/US2013/052799, filed Jul. 31, 2012, To—owned by Applicant.
Written opinion and search report for PCT/US2013/052799, filed Dec. 2, 2012, To—owned by Applicant.
PCT/US2013/073435 Published as WO 2014/093136, filed Dec. 5, 2013, To—owned by Applicant.
Written opinion and search report for PCT/US2013/073435, filed Apr. 30, 2012, To—owned by Applicant.
PCT/US2014/054437, filed Feb. 26, 2014, To—owned by Applicant.
Written opinion and search report for PCT/US2014/054437, filed Jan. 6, 2015, To—owned by Applicant.
PCT/US2016/014100, filed Dec. 17, 2015, To—owned by Applicant.
Written opinion and search report for PCT/US2016/014100, filed Jan. 6, 2015, To—owned by Applicant.
PCT/US2017/52708, filed Sep. 21, 2017, To—owned by Applicant.
Written opinion and search report for PCT/US2017/052708, filed Sep. 21, 2017, To—owned by Applicant.
PCT/US2016/053467 Published as WO 2017/053813, filed Sep. 24, 2015, Geist—owned by Applicant.
Written opinion and search report for PCT/US2016/053467, filed Sep. 24, 2015, Geist—owned by Applicant.
PCT/US2018/13207 Published as WO 2018/132502, filed Jan. 10, 2018, Shoshtaev—owned by Applicant.
Written opinion and search report for PCT/US2018/13207, filed Jan. 10, 2018, Shoshtaev—owned by Applicant.
PCT/US2018/43517, filed Jul. 24, 2018, To—owned by Applicant.
Written opinion and search report for PCT/US2018/43517, filed Jul. 24, 2018, To—owned by Applicant.
PCT/US2019/20354, filed Mar. 1, 2018, Shoshtaev—owned by Applicant.
Written opinion and search report for PCT/US2019/20354, filed Mar. 1, 2018, Shoshtaev—owned by Applicant.
European search report for EP 13862126, dated Dec. 5, 2013, To—owned by Applicant.
European search report for EP 14842880, dated Jun. 22, 2016, To—owned by Applicant.
European search report for EP 16740662, dated Nov. 29, 2017, To—owned by Applicant.
European search report for EP 17853887.2, dated Jul. 31, 2019, To—owned by Applicant.
European search report for EP 18738659.4, dated Jan. 10, 2018, Shoshtaev—owned by Applicant.
European search report for EP 19162909.6, dated Dec. 5, 2013, To—owned by Applicant.
JP 2009/505686 Comulative of WO 2007/009107, Jul. 14, 2005, Greenhalgh, et al.
Basho, R. et al. Lateral interbody fusion: Indications and techniques. Operative techniques in orthopaedics 21(3): 204-207 (Sep. 2011).
Caliber, www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].
Capstone® Peek spinal system PLIF anf TLIF surgical technique. Medtronic Sofamor Danek 1-36 (2009).
Coalign. Introducing AccuLIF expandable lumbar interbody fusion technology. [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
"Integrity Implants" (Integrity Implants) URL: http://www.integrityimplants.com/ [retrieved from internet Sep. 17, 2018].
"Integrity Implants v3" (Integrity Implants) URL: https://vimeo.com/232697959 ; [retrieved from the internet Nov. 16, 2017].
Interbody Fusion Cage (Neo IC) Source, www.tradekorea.com [online] URL: http://www.tradekorea.com/product-detail/P00015150/lnterbody_Fusion_Cage_Neo_IC_.html [retrieved Feb. 13, 2013].

(56) References Cited

OTHER PUBLICATIONS

Kaech, D.L. et al. Spinal restabilization procedures, diagnostic and therapeutic aspects of intervertebral fusion cages, artificial discs and mobile implants. Elsevier Science B.V. Part II: 121-204(2002).

Kiapour, A. et al. A biomechanical finite element study of subsidence and migration tendencies in stand-alone fusion procedures—comparison of an in situ expandable device with a rigid device. J Spine 1(4): 5 pages (2012).

Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].

Powerbuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].

PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].

Sasani, M. et al. Single-stage posterior corpectomy and expandable cage placement for treatment of thoracic or lumbar burst fractures. Spine 34(1): E33-E40 (Jan. 1, 2009).

Spineology. OptiMesh 1500E deploying grafting system. [online] URL: http://www.spineology.com/fb/intl/products/products/optimesh 1500e.html (retrieved Jun. 3, 2013).

STAXX XD, www.spinewave.com. [online] URL: http://www.spinewave.com/products/xd_us.html [retrieved on Jan. 27, 2013].

SynFix-LR System. Instruments and implants for stand-alone anterior lumbar interbody fusion (ALIF). Synthes SynFix-LR system technique guide 52 pages (2010).

Transforaminal Lumbar Interbody Fusion (TLIF). Virgina spine institute, Reston Virgina. [online] URL: http://www.spinemd.com/operative-treatments/tlif-transforaminal-lumbat-interbody-fusion.com 1-6 (2013). [retrieved on Jun. 16, 2013].

Uchida, K. et al. Anterior expandable strut cage replacement for osteoporotic thoracolumbar vertebral collapse. J Neurosurg Spine 4(6): 454-462 (Jun. 2006).

Xenos. Cage mesh system for spine. Biotek Chetan Meditech Pvt. Ltd. [online] URL: http://www.biotekortho.net/spine-treatment.html [retrieved on Feb. 13, 2013].

Zeus-O, [online] URL: http://www.amendia.com/zeuso.html [retrieved on Jan. 27, 2013].

* cited by examiner

SURGICAL IMPLANT AND RELATED METHODS

CROSS-REFERENCES TO RELATED APPLICATIONS

This application is a national stage application, filed under 35 U.S.C. 371, of international application no. PCT/US2018/043517, filed Jul. 24, 2018, which claims the benefit of U.S. provisional application No. 62/536,335, filed Jul. 24, 2017, each application of which is hereby incorporated herein by reference in its entirety.

FIELD

The present disclosure relates generally to the field of medical devices, and more specifically to expandable intervertebral implants.

BACKGROUND

The disc space or intervertebral space needs to be stabilized after the core of the disc is removed in a spinal fusion procedure. The emptied disc space is often larger than the size of the access corridor, and thus the fusion implants that are typically used are too small to fill the entire disc space. This may result in long-term instability. Ideally, the fusion implant is large enough in width to fill the disc space and as wide as possible to distribute the high compressive in vivo load over a larger area to avoid subsidence which leads to instability. Furthermore, spinal fusion implants sometimes back out of the disc over time after surgery and this can cause harm to the patient. Therefore it is desired that there is an implant that can collapse to a small size to be inserted through a small access opening in the patient, and then expand both vertically and horizontally to fill up the disc space as much as possible and in effect render a more stable fusion implant long-term as well as one that does not back out because it is expanded larger than the access corridor. Oftentimes, the opening in the disc (called an annulotomy) has the height of the space between the vertebra but has a width that is much smaller than the width of the space inside the disc. The ability to expand horizontally helps to make it more difficult for the implant to back out of the disc. During the horizontal expansion step, the inserter that holds the implant can be pushed towards sensitive anatomical structures such as nerves. There are no implants on the market that can expand horizontally and vertically while maintaining good strength and stability long-term while avoiding instrument shifting during expansion that may impinge on sensitive anatomy like nerves.

Furthermore, because so many different widths and heights are needed for a conventional implant, it is not cost effective to mold because of need develop so many expensive molds. Machining is there for used but is less consistent, reliable and expensive.

Existing spinal fusion implants are either made of a polymer such as Polyether Ether Ketone (PEEK), metal such as titanium, or ceramic such as silicon nitride. Some are made by a combination thereof. Some implants are made of PEEK coated with metal particles such as titanium or silver based due to the belief that the metal coatings are more osteogenic. However, the coatings can slough off from shear during implantation or in vivo and can cause adverse reactions. Also the implant is mostly radiolucent so it is hard to visualize on x-ray the full extent of the implant profile. Some implants are made of all metal or ceramics. These implants have shown improvement in surface fusion but they are both more stiff than bony endplate and can cause stress shielding. The all-metal implants are radiopaque for the most part and makes it hard to visualize bony fusion through the center of cage on post-operative follow up scans. There are implants made of PEEK in the middle with endplates that are slabs of porous metal. These are machined and assembled. Due to the aforementioned problems presented, there is a need for an implant that is expandable in 2 or more directions and with bone like stiffness and highly osteogenic surface interfacing with the endplate. It should also be designed to enable highly repeatable and cost effective fabrication methods.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein.

SUMMARY

Figure 1:
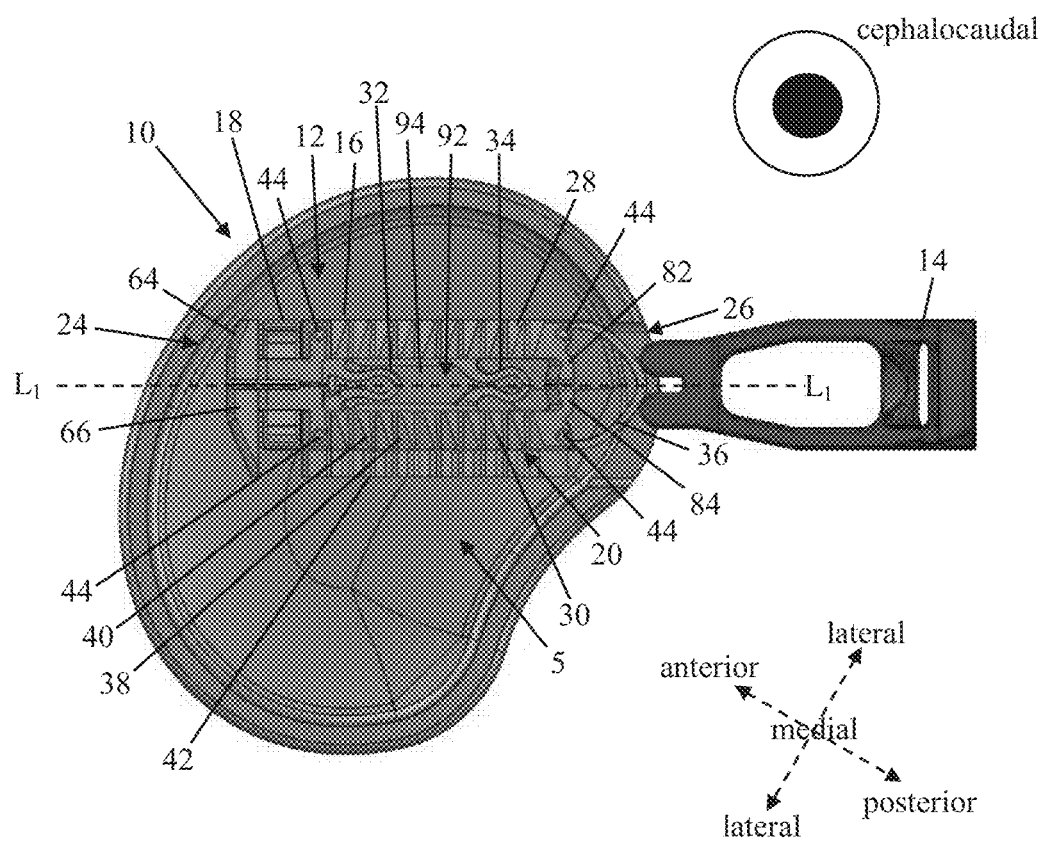
FIG. 1 is a plan view, a transverse section, of one example of a surgical implant showing a collapsed shell assembly inserted within a prepared intervertebral disc space, prior to insertion of the shim, according to an embodiment.

The teachings provided herein include expandable intervertebral implants. In some embodiments, a surgical implant configured for placement within an intervertebral space of a subject is provided.

The surgical implant can include, for example, a laterovertically-expanding shell configured to create an intervertebral scaffolding system in vivo, the shell having a first body portion configured to engage a first vertebral endplate and a second body portion configured to engage a second vertebral endplate, the shell further including a collapsed state and an expanded state; a guide element that slideably engages with the distal region of the shell, and is configured for retaining the shell from lateral movement that exceeds the expanded state; and a shim configured for in vivo introduction into the shell when the shell is in a collapsed state and thereafter causing expansion of the shell to an expanded state, the expansion occurring in a lateral direction and a vertical direction; wherein the shell is configured to extend asymmetrically in the lateral direction.

In some embodiments, the first body portion includes a first elongated support beam extending parallel to a first longitudinal axis of the shell, a second elongated support beam laterally displaced from the first elongated support beam and extending parallel to the longitudinal axis, and a plurality of connectors extending between and the first and second elongated support beams. In some embodiments, the second body portion includes a third elongated support beam extending parallel to a second longitudinal axis of the shell, a fourth elongated support beam laterally displaced from the third elongated support beam and extending parallel to the longitudinal axis, and a plurality of connectors extending between and the third and fourth elongated support beams.

In some embodiments, one of the first and second support beams includes a first lateral extension element extending in a direction away from the other of the first and second support beams, the first lateral extension element having a length dimension extending at least substantially the length of the respective support beam and a width dimension extending laterally away from the edge of the respective support beam. In some embodiments, one of the third and fourth support beams includes a second lateral extension element extending in a direction away from the other of the third and fourth support beams, the second lateral extension element having a length dimension extending substantially the length of the respective support beam and a width dimension extending laterally away from the edge of the respective support beam. In some embodiments, the first and second lateral extension elements extend in the same direction.

In some embodiments, the respective support beams having the first and second lateral extension elements each have a width dimension that is between 1.2 and 10 times greater than the width dimensions of the other respective support beams.

The shell can comprise structural elements that are interconnected, for example, using connectors. The connectors can be bowed, for example, in a proximal direction. In some embodiments, the bowed connectors maintain a curved orientation at the apex of the bowed shape to prevent, or at least inhibit, any stress cracking that may otherwise occur.

The shell can be made of a combination of materials that are combined in layers to impart desired physical characteristics to the implant. In some embodiments, the shell can be made from at least one of a polymer, metal alloy, and titanium alloy. In some embodiments, the shell includes a central layer and a plurality of surface layers, the central layer and surface layers comprising different materials. In some embodiments, the central layer is made from a medical grade polymer. In some embodiments, the medical grade polymer is one of PEEK, polyetherimide, polyimide, and polyamide. In some embodiments, the surface layers are made from at least one of titanium alloy, cobalt chromium, stainless steel, ceramic, silicon nitride, and hydroxyapatite.

As such, in some embodiments, the laterovertically expanding shell can be configured to create an intervertebral scaffolding system in vivo, the shell having a first body portion configured to engage a first vertebral endplate and a second body portion configured to engage a second vertebral endplate, the shell further including a collapsed state and an expanded state; a guide element that slideably engages with the distal region of the shell, and is configured for retaining the shell from lateral movement that exceeds the expanded state; and a shim configured for in vivo introduction into the shell when the shell is in a collapsed state and thereafter causing expansion of the shell to an expanded state, the expansion occurring in a lateral direction and a vertical direction; wherein the shell includes a central layer and a plurality of surface layers, the central layer and surface layers comprising different materials. The central layer can be made from a medical grade polymer, for example. In some embodiments, the medical grade polymer can include one of PEEK, polyetherimide, polyimide, and polyamide. The surface layers can be made from at least one of titanium alloy, cobalt chromium, stainless steel, ceramic, silicon nitride, and hydroxyapatite. The surface layers can have at least one of a roughened and porous texture. And, in some embodiments, the surface layers are associated with the central layer using at least one of pressure, heat melting, snap fit engagement, and adhesive.

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical implant and related methods disclosed herein boasts a variety of inventive features and components that warrant patent protection, both individually and in combination.

The surgical implants can be specifically configured to have a shape upon expansion that is asymmetric within the intervertebral space. For example, the surgical implant can be biased in shape, extending further in a first lateral direction than in a second lateral direction to bias the profile, or footprint, of the surgical implant in the first lateral direction in the intervertebral space. This asymmetry can, for example, provide additional scaffolding support to vertical forces in the intervertebral space and/or prevent, or at least inhibit, a migration of the surgical implant in the intervertebral space after implanting it in the subject. The asymmetric shape can be biased in any direction desired including, but not limited to, a direction that is on a side of the implant positioned medial in an intervertebral space, a direction that is on a side of the implant positioned posterior in an intervertebral space, a direction that is on a side of the implant positioned anterior in an intervertebral space, or a direction that is on a side of the implant positioned lateral in an intervertebral space, or a direction representing an orientation that is a combination thereof.

In some embodiments, the surgical implant can include, for example, a laterovertically-expanding shell configured to create an intervertebral scaffolding system in vivo, the shell having a first body portion configured to engage a first vertebral endplate and a second body portion configured to engage a second vertebral endplate, the shell further including a collapsed state and an expanded state; a guide element that slideably engages with the distal region of the shell, and is configured for retaining the shell from lateral movement that exceeds the expanded state; and, a shim configured for in vivo introduction into the shell when the shell is in a collapsed state and thereafter causing expansion of the shell to an expanded state, the expansion occurring in a lateral direction and a vertical direction; wherein the shell is configured to extend asymmetrically in the lateral direction.

One of skill will appreciate that the terms "lateral", "vertical", and "laterovertical" can be used as terms of relative orientation, meaning that the surgical implant can expand in at two directions that are normal to each other. In some embodiments, the term "vertical" can be used herein synonymously with "cephalocaudal", "craniocaudal", and the like, meaning that the implant expands at least substantially in the vertical direction of the spine, at least substantially in the directions of the coronal and sagittal planes of the subject, expanding the intervertebral space by applying a force to the two vertebral endplates that define the upper and lower borders of the intervertebral space. In some embodiments, the term "lateral" can be used herein synonymously with the term "transverse", which encompasses the terms "mediolateral", "anteromedial", posteromedial", and the like, meaning that the implant expands in any direction that is at least substantially in the direction of a transverse plane of the subject. This can include, for example, expanding the implant toward the annular walls of the disc space, in some embodiments, and away from the annular walls in some embodiments. Likewise, the term "laterovertical" can be used, for example, to refer to an expansion that is at least substantially in the "cephalocaudal" or "craniocaudal" direction combined with an expansion that is at least substantially in the direction of a transverse plane, noting that the transverse plane can be used relative to the subject as a whole, or relative to an anatomical position within the subject, which transverse plane relative to the anatomical position can vary a bit in direction due to normal anatomical variation, or perhaps a disease or disorder.

The term "at least substantially" will be understood by those of skill in the art as a term that provides for some variance from a strict and narrowly construed direction, essentially meaning "generally in that direction" or "generally in that orientation". This is because, although the orientation of the implant or its movement is intended to be in a particular direction, a pure orientation or direction is often not reasonable to expect in practical application within a subject, and a reasonable amount of deviation in that direction is understood and acceptable by those of skill for the purposes of understanding the scope of, and practicing, the teachings provided herein. In some embodiments, for example, an orientation is at least substantially on a plane or a direction when it's orientation deviates from the plane or direction by no more than 40%, no more than 30%, no more than 20%, no more than 10%, no more than 5%, no more than 1%, or no more than any amount or range therein in increments of 0.1%. In some embodiments, the vertical expansion of the vertebral implant in an intervertebral space can occur, for example, in a direction that is stil "craniocaudal" and is understood to be at least substantially parallel to the vertical axis of the intervertebral disc space, for example, such that the vertical axis of the intervertebral disc space is defined by a line connecting the center of the top vertebral endplate and the center of the bottom vertebral endplate defining that intervertebral space when combined with the annulus surrounding the space. Likewise, in some embodiments, the lateral expansion of the vertebral implant in an intervertebral space can occur, for example, in a direction that is at least substantially parallel to any direction of a transverse plane through the intervertebral disc space. In some embodiments, the transverse plane of the intervertebral disc space can be defined by a transverse section of the annulus of the disc rather than a transverse section of the subject, the transverse plane being placed equidistant between the top vertebral endplate and the bottom vertebral endplate, the transverse section of the disc space varying from a transverse section of the subject as a whole, as it is tilted to account for any lordosis, kyphosis, scoliosis, or bone degeneration or disease which can alter the relative position of the intervertebral space within the subject from an otherwise pure interpretation of the orientation intended.

In some embodiments, the first body portion includes a first elongated support beam extending at least substantially parallel to a first longitudinal axis of the shell, a second elongated support beam laterally displaced from the first elongated support beam and extending at least substantially parallel to the longitudinal axis, and a plurality of connectors extending between and the first and second elongated support beams. In some embodiments, the second body portion includes a third elongated support beam extending at least substantially parallel to a second longitudinal axis of the shell, a fourth elongated support beam laterally displaced from the third elongated support beam and extending at least substantially parallel to the longitudinal axis, and a plurality of connectors extending between and the third and fourth elongated support beams. In some embodiments, the first longitudinal axis of the shell can be at least substantially parallel to the second longitudinal axis. And, in some embodiments, the first longitudinal axis can be at least substantially coincident with the second longitudinal axis. In embodiments where the first longitudinal axis is at least substantially coincident with the second longitudinal axis, this can be referred to as a central, longitudinal axis. In some embodiments, the central longitudinal axis can be identified as being at least substantially central to the positions of the first, second, third, and fourth support beams. In some embodiments, the central longitudinal axis can be identified as being at least substantially central to a lumen defined by the positions of the first, second, third, and fourth support beams.

In some embodiments, one of the first and second support beams includes a first lateral extension element extending in a direction away from the other of the first and second support beams, the first lateral extension element having a length dimension extending at least substantially the length of the respective support beam and a width dimension extending laterally away from the edge of the respective support beam. In such embodiments, the first and second support beams can be oriented to a first plane, and the lateral extension element extends away from either the first or second support beam in a direction that is at least substantially parallel to the first plane and away from the other of the first and second support beams. Likewise, in some embodiments, one of the third and fourth support beams includes a second lateral extension element extending in a direction away from the other of the third and fourth support beams, the second lateral extension element having a length dimension extending substantially the length of the respective support beam and a width dimension extending laterally away from the edge of the respective support beam. Likewise, the third and fourth support beams can be oriented to a second plane, and the lateral extension element extends away from either the third or fourth support beam in a direction that is at least substantially parallel to the second plane and away from the other of the third and fourth support beams. In some embodiments, the first and second lateral extension elements extend at least substantially in the same direction.

In some embodiments, the respective support beams having the first and second lateral extension elements each have a width dimension that is at least 20% greater than the other to provide an asymmetrical extension of the shell in the desired direction in an intervertebral space. In some embodiments, the width of a support can range from about 1.2 to about 10 times greater than the width dimension of the other respective support beam, or any range therein. In some embodiments, the lateral extension element of one beam can be about 1.2, about 2x, about 3x, about 4x, about 5x, about 6x, about 7x, about 8x, about 9x, or about 10x, or any amount or range therein in increments of 0.1x, greater than the other support beam in order to create the desired asymmetry or bias of the surgical implant. In some embodiments, the extension is at least substantially as long as the support beam from which it extends. In some embodiments, a plurality of extensions are provided from the support beam, rather than a single extension.

The shell can comprise structural elements that are interconnected, for example, using connectors. In some embodiments, the connectors are flexible and configured for expansion and collapse of the shell. The connectors can be referred to as struts, in some embodiments. The connectors can be bowed, for example, in a proximal direction or a distal direction. In some embodiments, the bowed connectors maintain a curved orientation at the apex of the bowed shape to prevent, or at least inhibit, any stress cracking that may otherwise occur. In some embodiments, the connectors flex in, on, or at least substantially parallel to, a plane that intersects the longitudinal axes of the support beams that are interconnected by the connectors.

The shell can be made of a combination of materials that are combined in layers to impart desired physical characteristics to the implant, such as a particular configuration that imparts a desired strength, rigidity, flexibility, friction, biocompatibility, and/or osteogenecity, ease of manufacture, and the like, or any combination thereof, to any one or any combination of elements that compose the shell. In some embodiments, the shell is made from at least one of a polymer, metal alloy, and titanium alloy. In some embodiments, a first layer of the shell can comprise a polymer, a second layer can comprise a metal, and the first and second layers can be adjacent to one another. In some embodiments, a first layer of the shell can comprise a first polymer, a second layer can comprise a second polymer, and the first and second layers can be adjacent to one another. In some embodiments, a first layer of the shell can comprise a first metal, a second layer can comprise a second metal, and the first and second layers can be adjacent to one another. In some embodiments, the shell includes a central layer and a plurality of surface layers, the central layer and surface layers comprising different materials. In some embodiments, the central layer is made from a medical grade polymer. In some embodiments, the medical grade polymer is one of PEEK, polyetherimide, polyimide, and polyamide. In some embodiments, the surface layers are made from at least one of titanium alloy, cobalt chromium, stainless steel, ceramic, silicon nitride, and hydroxyapatite.

As such, in some embodiments, the laterovertically expanding shell is configured to create an intervertebral scaffolding system in vivo, the shell having a first body portion configured to engage a first vertebral endplate and a second body portion configured to engage a second vertebral endplate, the shell further including a collapsed state and an expanded state; a guide element that slidably engages with the distal region of the shell, and is configured for retaining the shell from lateral movement that exceeds the expanded state; and a shim configured for in vivo introduction into the shell when the shell is in a collapsed state and thereafter causing expansion of the shell to an expanded state, the expansion occurring in a lateral direction and a vertical direction; wherein the shell includes a central layer and a plurality of surface layers, the central layer and surface layers comprising different materials. The central layer can be made from a medical grade polymer, for example. In some embodiments, the medical grade polymer can include one of PEEK, polyetherimide, polyimide, and polyamide. The surface layers can be made from at least one of titanium alloy, cobalt chromium, stainless steel, ceramic, silicon nitride, and hydroxyapatite.

In any of the embodiments taught herein, the implant can have surface layers with at least one of a roughened and porous texture, for example, which can impart a morphology having a desired characteristic including, but not limited to, osteogenesis, osteoinduction, osteointegration, and an increase in implant surface area which can be used to facilitate the same. And, in some embodiments, the surface layers are associated with the central layer using at least one of pressure, heat melting, snap fit engagement, and adhesive.

FIGS. 1-13 illustrate an example of a surgical implant 10, according to an embodiment. By way of example, the surgical implant 10 of the present disclosure is a spinal fusion implant that may be inserted into an intervertebral disc space during a minimally invasive or open spinal fusion surgery, from any suitable approach (e.g. anterior, posterior, lateral, postero-lateral, etc). After insertion into the disc space, the surgical implant 10 of the present disclosure is expandable in multiple directions (e.g. vertically and laterally) to create an improved footprint within the disc space, which in turn enhances the stability of the fusion surgery. Multiple graft windows allow for the use of bone graft material (e.g. biologic bone, artificial bone matrix, collagen, protein, etc.). By way of example, the surgical implant 10 of the present disclosure includes a multi-axially expandable, unibody structure having a generally rectangular cross-sectional shape and a central longitudinal axis $L_1$ parallel to a long edge of the implant 10. The surgical implant 10 of the present example includes a shell assembly 12 that is inserted into a surgically prepared target disc space and a shim 14 that is thereafter inserted into the shell assembly 12 to facilitate expansion of the shell assembly 12 within the target disc space. When fully inserted into the shell assembly 12, the shim 14 securely couples with the shell assembly 12 to provide stability to the expanded construct.

Figure 2:
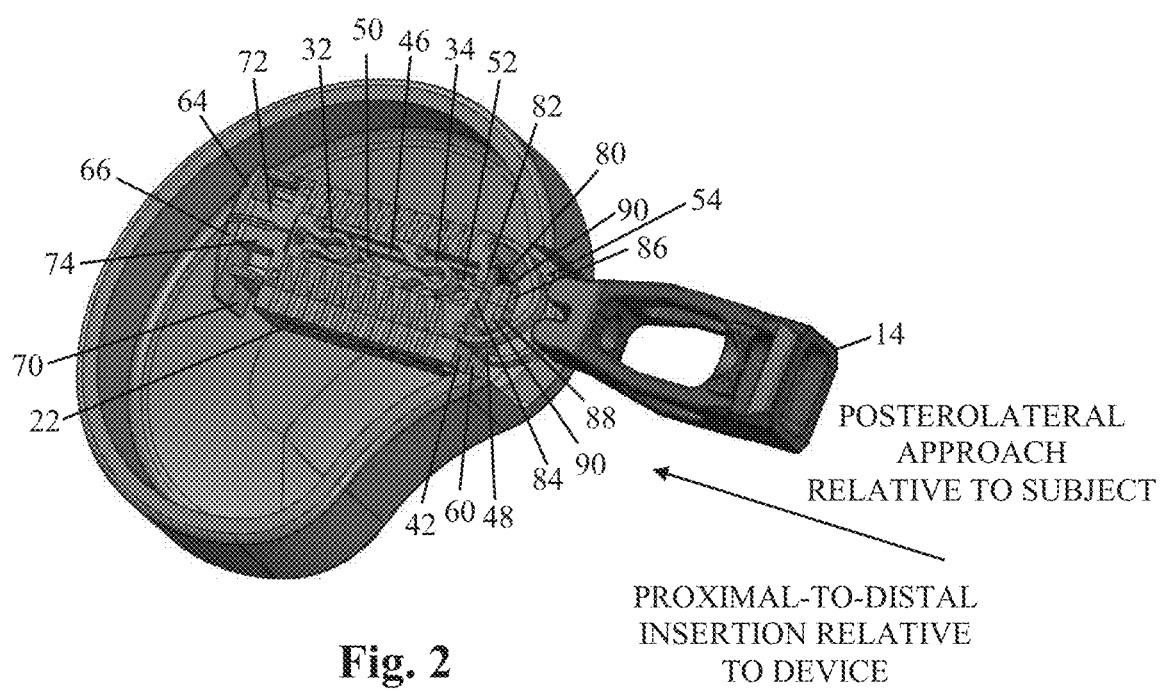
FIG. 2 is a perspective view of the surgical implant of FIG. 1.
Figure 3:
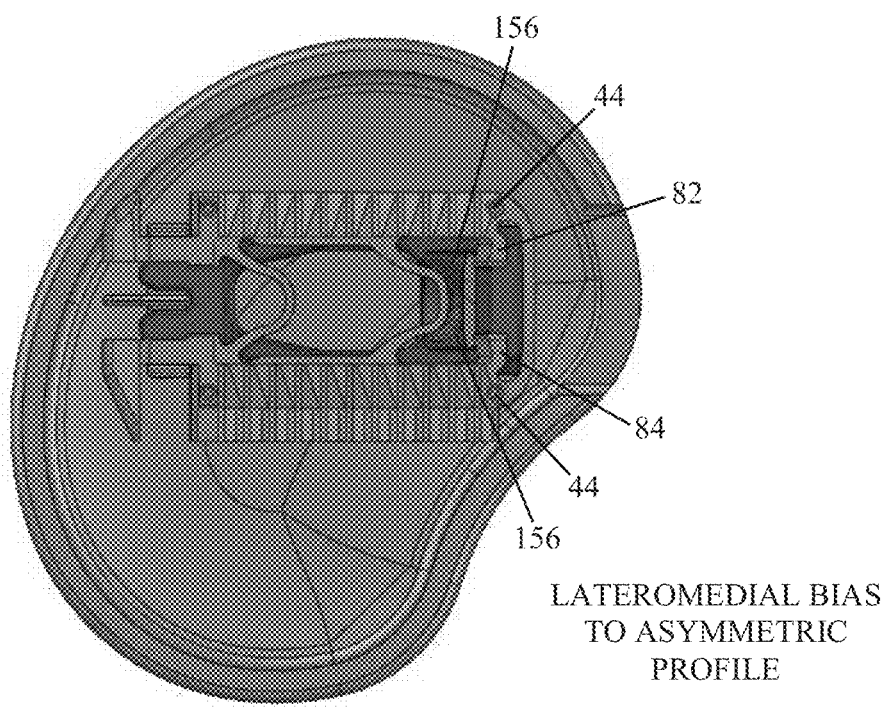
FIG. 3 is a plan view, a transverse section, of the surgical implant of FIG. 1 with the shim fully inserted into the shell.
Figure 4:
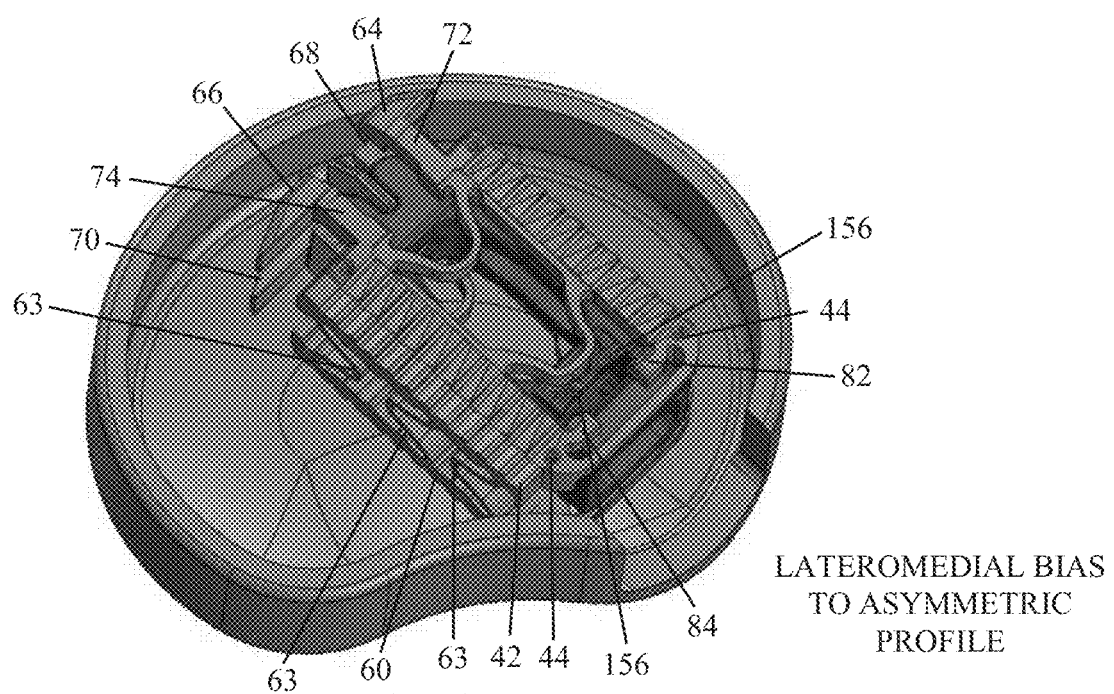
FIG. 4 is a perspective view of the surgical implant of FIG. 3.

FIGS. 1-2 illustrate a collapsed shell assembly 12 inserted within a transverse section of a prepared intervertebral disc space 5, prior to insertion of the shim 14, while FIGS. 3-4 illustrate an expanded shell assembly 12 within the disc space 5 with the shim 14 fully inserted. FIG. 1 shows the relative orientation of the view within the subject receiving the implant, illustrating the cephalocaudal (or craniocaudal) directions, as well as the anterior, posterior, medial, and lateral directions within the subject. FIG. 2 shows the posterolateral approach that is used to insert the implant, relative to the orientation of the subject, as well as the proximal-to-distal insertion of the implant, relative to the orientation of the implant itself. FIGS. 3 and 4 show the lateromedial bias to the asymmetric profile of the implant, relative to the orientation of the subject. By way of example, the shell assembly 12 includes a shell 16 and a guide element 18. The shell 16 includes a first body portion 20, second body portion 22, leading (or "distal") end 24, and a trailing (or "proximal") end 26. When the surgical implant 10 has been implanted within an intervertebral disc space, the first body portion 20 will contact an endplate of a first vertebral body and the second body portion 22 will contact an endplate of a second vertebral body. To clarify the orientation of the implantation relative to the subject and the implant description, FIG. 1 shows a posterolateral approach relative to the subject but a proximal-to-distal insertion of the device, the implant extended with a medial, or posteromedial, bias, as used herein.

The first body portion 20 includes a first elongated support beam 28 extending parallel to the longitudinal axis $L_1$, a second elongated support beam 30 extending parallel to the longitudinal axis $L_1$, and a plurality of flexion struts extending between and connecting the first and second elongated support beams 28, 30. The example shown by way of illustration includes first and second flexion struts 32, 34 positioned directly between the first and second support beams 28, 30, and a third flexion strut 36 positioned at the trailing end 26, however any number of flexion struts may be used. Each of the first and second elongated support beams 28, 30 includes an outer surface 38 adapted to interface with the body tissue (e.g. vertebral endplate). The outer surface 38 may include any number of anti-migration features 40 to ensure the implant 10 remains in place after insertion into the patient's intervertebral disc space. By way of example, the anti-migration features 40 may include a plurality of teeth (see e.g. FIG. 1), spikes, surface roughening, friction elements, and the like.

The second elongated support beam 30 includes a lateral extension 42 that extends away from the longitudinal axis $L_1$ of the implant 10. The lateral extension 42 expands the width dimension of the second elongated support beam 30, enabling it to protrude into the disc space 5 (after insertion) to expand the footprint of the implant 10 within the disc space, giving further stability to the implanted construct. For example, for a posterior or posterolateral approach (such as the one shown by way of example in FIG. 1), the increased wall thickness/lateral extension 42 is on the medial side. When the shim 14 is inserted to expand the shell 16 (FIGS. 3-4), the shell 16 (or footprint thereof) can extend asymmetrically such the medial side expands more than the lateral side due to the thicker wall/lateral extension. Since the shell 16 extends more medially than laterally within the disc space, the shim 14 and insertion instrument (not shown) do not require repositioning in the body during placement, and are thus less likely to impinge upon adjacent nerve structure (for example the dura sac). Furthermore, by extending more medially, the implant 10 is positioned more centrally within the disc space, which is preferable for support of the disc for fusion purposes. By way of example, the thicker side (e.g. the second elongated support beam 30 with lateral extension 42/increased thickness) may have a width dimension that is 1.2-10 times greater than the width dimension of the first elongated support beam 28.

In the current example embodiment, the shell 16 is made from polyetheretherketone (PEEK), however any suitable medical grade material may be used to manufacture the shell 16, including but not limited to polymers (e.g. PEEK, polyetherimide (Ultem), polyimide, polyamide), metal alloys (e.g. cobalt chromium), and/or titanium alloys (e.g. Ti6Al4V, nickel titanium). In instances in which a radiolucent polymer (e.g. PEEK) is used, the implant may not be visible during fluoroscopic imaging (during surgery or post-op). Thus, a plurality of radiographic markers 44 may be embedded within the first body portion to aid with intraoperative (and post-operative) visibility of the implant, to ensure proper positioning and locking of the final construct before completion of the surgery. By way of example, the radiographic markers 44 are positioned near the proximal and distal ends of the first and second elongated support beams 28, 30, as shown in FIG. 1. The radiographic markers 44 may be made from any suitable radiopaque material (e.g. titanium, tantalum, etc).

The first and second flexion struts 32, 34, extend between the first and second support beams 28, 30, however each of the flexion struts 32, 34 has a length that is greater than the distance between the first and second support beams 28, 30. As such, the flexion struts 32, 34 are bowed in a proximal direction to fit between the support beams 28, 30 without breaking the plane of the support beams 28, 30. The bowed flexion struts 32, 34 maintain a curved orientation at the apex of the bowed shape (as opposed to a sharp angle), which is located at the midpoint of the distance between the first and second support beams 28, 30, to prevent stress cracking. By way of example, the bowed shape may be generally "U"-shaped, "C"-shaped, "S"-shaped, "W"-shaped, or sinusoidal. The flexion struts 32, 34 are generally uniform in thickness in the proximal-distal direction however the strut thickness may be increased at either end of the struts near the junctions with the first and second support beams 28, 30. By way of example, the strut thickness in the proximal-distal direction of the shell may be between 0.1-2 mm and preferably 0.2-1 mm. This amount of thickness allows for bending of the struts during collapsing or expansion of the shell 16 without excessive strain on the struts. The struts 32, 34 may have a thickness in the range of 2-12 mm in the transverse direction (perpendicular to the proximal-distal axis). This increased thickness in the transverse direction is desired to maintain a high structural stiffness and strength in the transverse direction so that the transverse cross section shape is maintained during and after insertion into the disc space, during implant expansion when the shim 14 is inserted into the shell 16, and after the surgery when the patient resumes normal activity.

The third flexion strut 36 is attached at either end to the proximal ends of the first and second support beams 28, 30. As with the first and second flexion struts 32, 34, the third flexion strut 36 has a length that is greater than the distance between the first and second support beams 28, 30. As such, the third flexion strut 36 is bowed in a proximal direction. By way of example, a "bowed" shape may be generally "U"-shaped, "C"-shaped, "S"-shaped, "W"-shaped, or sinusoidal. The flexion strut 36 can be uniform in thickness in the proximal-distal direction however the strut thickness may be increased at either end of the strut near the junctions with the first and second support beams 28, 30. By way of example, the third strut 36 may have similar thickness in the proximal-distal direction and transverse direction as described above in reference to the first and second flexion struts 32, 34. In some embodiments, the flexion strut 36 can be configured to maintain a curved orientation at the apex of the bowed shape to prevent stress cracking, and in some embodiments, the third flexion strut 36 can be designed to be drawn to a tension upon expansion, and it can be configured to be elastic or inelastic.

In some embodiments, the second body portion 22 can be essentially a mirror image copy of the first body portion 20. It should be understood, for example, that all of the features described above in relation to the first body portion 20 can be included in mirror image fashion on the second body portion 22. The second body portion 22 can include a third elongated support beam 46 extending parallel to the longitudinal axis $L_1$, a fourth elongated support beam 48 extending parallel to the longitudinal axis $L_1$, and a plurality of flexion struts extending between and connecting the third and fourth elongated support beams 46, 48. The example shown by way of illustration includes first and second flexion struts 50, 52 positioned directly between the third and fourth support beams 59, 52, and a third flexion strut 54 positioned at the trailing end 26, however any number of flexion struts may be used. Each of the third and fourth elongated support beams 46, 48 includes an outer surface 56 adapted to interface with the body tissue (e.g. vertebral endplate). The outer surface 56 may include a any number of anti-migration features 58 to ensure the implant 10 remains in place after insertion into the patient's intervertebral disc space. By way of example, the anti-migration features 58 may include a plurality of teeth (see e.g. FIG. 1), spikes, surface roughening, friction elements, and the like.

The fourth elongated support beam 48 in the current example includes a lateral extension 60 that extends away from the longitudinal axis $L_1$ of the implant 10. The lateral extension 60 expands the width dimension of the fourth elongated support beam 48, enabling it to protrude into the disc space 5 (after insertion) to expand the footprint of the implant 10 within the disc space, giving further stability to the implanted construct. For example, for a posterior or postero-lateral approach (such as the one shown by way of example in FIG. 1), the increased wall thickness/lateral extension 60 is on the medial side. When the shim 14 is inserted to expand the shell 16 (FIGS. 3-4), the shell 16 (or footprint thereof) can expand asymmetrically such the medial side expands more than the lateral side due to the thicker wall/lateral extension. Since the shell 16 extends more medially than laterally within the disc space in this embodiment, the shim 14 and insertion instrument (not shown) do not require repositioning with instruments in the body during placement, and are thus less likely to impinge upon adjacent nerve structure (for example the dura sac). Furthermore, by expanding more medially, the implant 10 is positioned more centrally within the disc space, which is preferable for support of the disc for fusion purposes. By way of example, the thicker side (e.g. the fourth elongated support beam 48 with lateral extension 60/increased thickness) may have a width dimension that is 1.2-10 times greater than the width dimension of the third elongated support beam 46.

A plurality of radiographic markers 62 may be embedded within the second body portion 22 to aid with intraoperative (and post-operative) visibility of the implant, to ensure proper positioning and locking of the final construct before completion of the surgery. By way of example, the radiographic markers 62 are positioned near the proximal and distal ends of the third and fourth elongated support beams 46, 48. The radiographic markers 62 may be made from any suitable radiopaque material (e.g. titanium, tantalum, etc).

The first and second flexion struts 50, 52 extend between the third and fourth support beams 46, 48, however each of the flexion struts 50, 52 has a length that is greater than the distance between the third and fourth support beams 46, 48. As such, the flexion struts 50, 52 are bowed in a proximal direction to fit between the support beams 46, 48 without breaking the plane of the support beams 46, 48. The bowed flexion struts 50, 52 maintain a curved orientation at the apex of the bowed shape (as opposed to a sharp angle), which is located at the midpoint of the distance between the third and fourth support beams 46, 48, to prevent stress cracking. By way of example, the bowed shape may be generally "U"-shaped, "C"-shaped, "S"-shaped, "W"-shaped, or sinusoidal. The flexion struts 50, 52 are generally uniform in thickness in the proximal-distal direction however the strut thickness may be increased at either end of the struts near the junctions with the third and fourth support beams 46, 48. By way of example, the first and second flexion struts 50, 52 of the second body portion 22 may have similar thickness in the proximal-distal direction and transverse direction as described above in reference to the first and second flexion struts 32, 34 of the first body portion 20.

The third flexion strut 54 of the second body portion 22 is attached at either end to the proximal ends of the third and fourth support beams 46, 48. As with the first and second flexion struts 50, 52, the third flexion strut 54 has a length that is greater than the distance between the third and fourth support beams 46, 48. As such, the third flexion strut 54 is bowed in a proximal direction. The bowed flexion strut 54 maintains a curved orientation at the apex of the bowed shape to prevent stress cracking. By way of example, the bowed shape may be generally "U"-shaped, "C"-shaped, "S"-shaped, "W"-shaped, or sinusoidal. The third flexion strut 54 is generally uniform in thickness in the proximal-distal direction however the strut thickness may be increased at either end of the strut near the junctions with the third and fourth support beams 46, 48. By way of example, the third flexion strut 54 of the second body portion 22 may have similar thickness in the proximal-distal direction and transverse direction as described above in reference to the first and second flexion struts 32, 34 of the first body portion 20.

The first and second body portions 20, 22 are connected to one another via a plurality of lateral flexion struts 63, as best viewed in FIG. 4. By way of example only, each side has a group of three lateral flexion struts 63, however more or less may be included without departing from the scope of this disclosure. One group of lateral flexion struts 63 extends between the first support beam 28 and the third support beam 46, and the other group of lateral flexion struts 63 extends between the second support beam 30 and the fourth support beam 48. Each of the flexion struts 63 has a length that is greater than the distance between the respective support beams. As such, the flexion struts 63 are bowed in either a proximal or distal direction to fit between the support beams without breaking the plane of the support beams. The bowed flexion struts 63 maintain a curved orientation at the apex of the bowed shape (as opposed to a sharp angle), which is located at the midpoint of the distance between the first and second body portions 20, 22, to prevent stress cracking. By way of example, the bowed shape may be generally "U"-shaped, "C"-shaped, "S"-shaped, "W"-shaped, or sinusoidal. The flexion struts 63 are generally uniform in thickness in the proximal-distal direction. By way of example, the strut thickness in the proximal-distal direction, or longitudinal thickness, may be between 0.1-2 mm and preferably 0.2-1 mm. This amount of thickness allows for bending of the struts during collapsing or expansion of the shell 16 without excessive strain on the struts. The struts 63 may have a thickness in the range of 2-12 mm in the transverse direction (perpendicular to the proximal-distal axis). This increased thickness in the transverse direction is desired to maintain a high structural stiffness and strength in the transverse direction so that the transverse cross section shape is maintained during and after insertion into the disc space, during implant expansion when the shim 14 is inserted into the shell 16, and after the surgery when the patient resumes normal activity. As taught herein, the ratio of longitudinal thickness to transverse thickness of the struts can be configured, in some embodiments, to add a particular strength to the connectors in order to maintain the shape of the shell.

In the current example, the leading end 24 comprises four distal panels 64, 66, 68, 70 that, while the implant 10 is in an initial, collapsed state (e.g. as it would be during the insertion process), are arranged in such close proximity to one another so as to create a solid wall at the leading end. Each of the four distal panels 64, 66, 68, 70 has a generally rectangular perimeter and is arranged perpendicular to the longitudinal axis $L_1$. Each of the four panels is integrally formed with an extension arm that extends distally from one of the aforementioned elongated support beams. For example, a first distal panel 64 is connected to the first elongated support beam 28 by way of a first extension arm 72. A second distal panel 66 is connected to the second elongated support beam 30 by way of a second extension arm 74. A third distal panel 68 is connected to the third elongated support beam 46 by way of a third extension arm 76. A fourth distal panel 70 is connected to the fourth elongated support beam 48 by way of a fourth extension arm 78. The distal panels 64, 66, 68, 70 each include a smooth outer leading surface that is at least partially tapered to provide for easier insertion into the disc space. When the implant is in the initial, collapsed state, the distal panels 64, 66, 68, 70 align with the central flange 106 of the guide element 18 to form a closed surface to prevent seepage of body fluids and/or tissue into the implant during insertion into the target disc space.

The trailing end 26 includes an aperture 80 that provides access to the central lumen 82 of the shell 16 when the implant is in a collapsed orientation, such as during insertion into the disc space. The aperture 80 is sized and configured to allow passage of any instrument used during insertion, including but not limited to an inserter, various cannula and the like, as well as graft material (e.g. biologic bone, synthetic bone matrix, collagen, protein, etc.) and the shim 14. As such, unlike the "closed" configuration of the leading 24 discussed above, the trailing end 26 has an "open" configuration. The trailing end 26 further comprises four medial flanges 82, 84, 86, 88 that, while the implant 10 is in an initial, collapsed state (e.g. as it would be during the insertion process), are arranged in such close proximity to one another so as to create a rigid crossbar at the trailing end 26 to increase implant stability. Each of the medial flanges 82, 84, 86, 88 is generally perpendicular to the longitudinal axis $L_1$ and extends inward relative to the implant. Each of the medial flanges 82, 84, 86, 88 is integrally formed with one of the aforementioned elongated support beams. For example, a first medial flange 82 extends from the first elongated support beam. The second medial flange 84 extends from the second elongated support beam 30. A third medial flange 86 extends from the third elongated support beam 46. A fourth medial flange 88 extends from the fourth elongated support beam 48. The medial flanges 82, 84, 86, 88 each include a smooth tapered surface 90 on the edge of the aperture 80 to provide for easier insertion of the shim 14 into the shell 16.

The shell 16 further includes a central lumen 92 and a plurality of graft windows 94. The central lumen 92 extends through the shell 16 and is sized and configured to allow passage of any instrument used during insertion, including but not limited to an inserter, various cannula and the like, as well as graft material (e.g. biologic bone, synthetic bone matrix, collagen, protein, etc.) and the shim 14. For example, the inserter passes through the aperture 80 and central lumen 92 and couples with the threaded post 102 of the guide element 18, which is positioned near the leading end 24 of the implant. The graft windows 94 are relatively large and enable fusion of the graft material with tissue.

Figure 5:
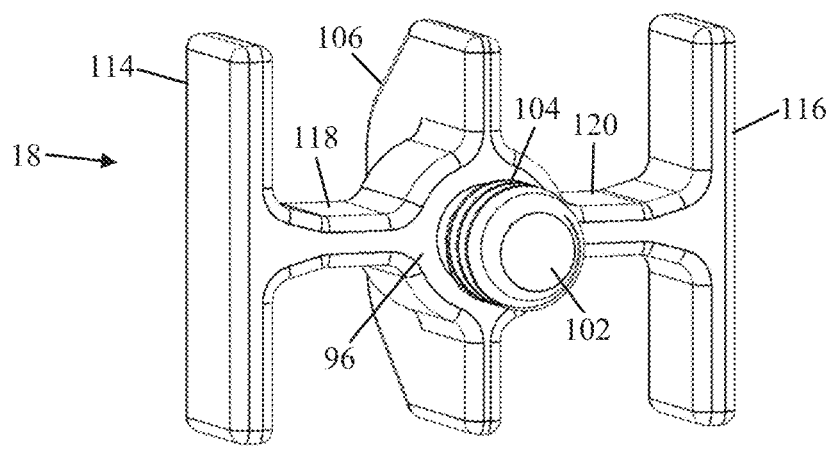
FIG. 5 is a perspective view of a guide element forming part of the surgical implant of FIG. 1.
Figure 6:
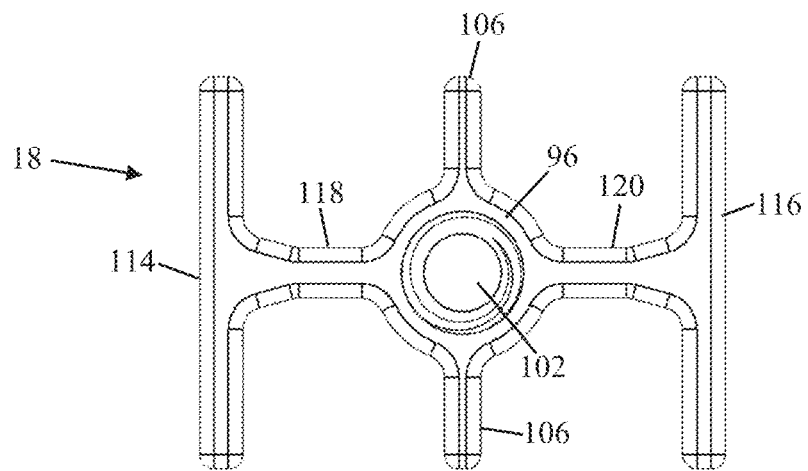
FIG. 6 is a plan view of the guide element of FIG. 5.
Figure 7:
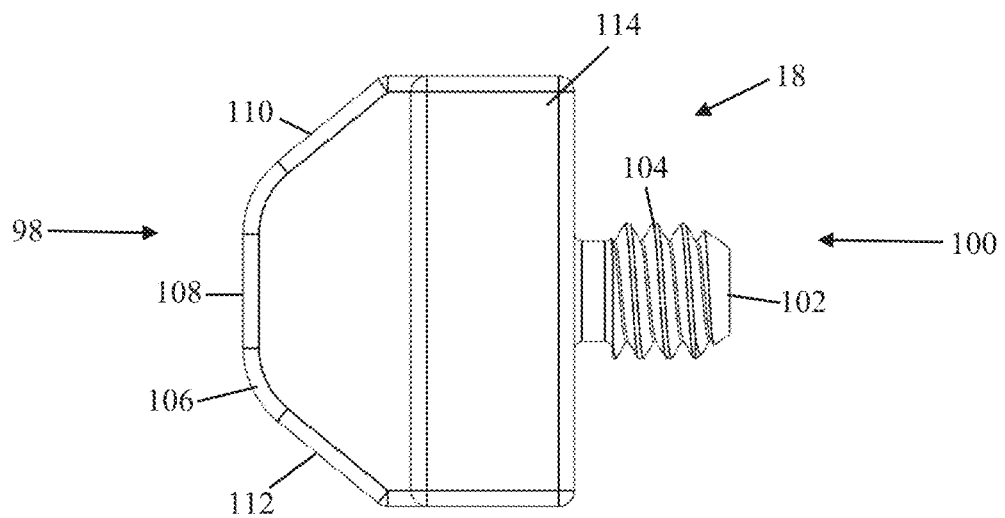
FIG. 7 is a side plan view of the guide element of FIG. 5.
Figure 8:
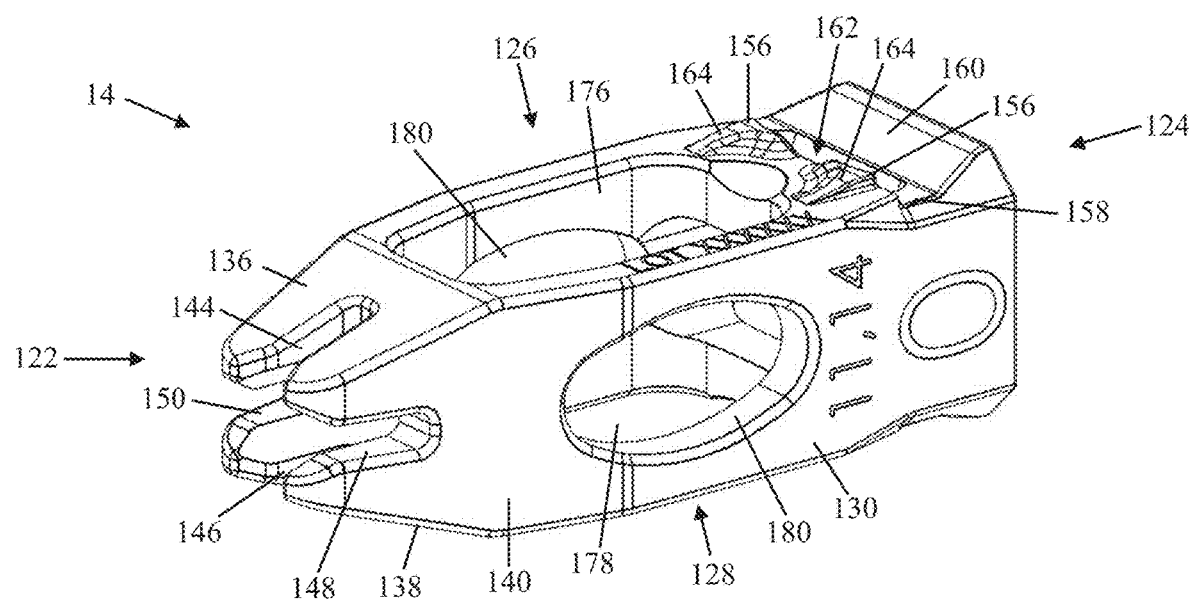
FIGS. 8-9 are perspective views of a shim forming part of the surgical implant of FIG. 1.
Figure 9:
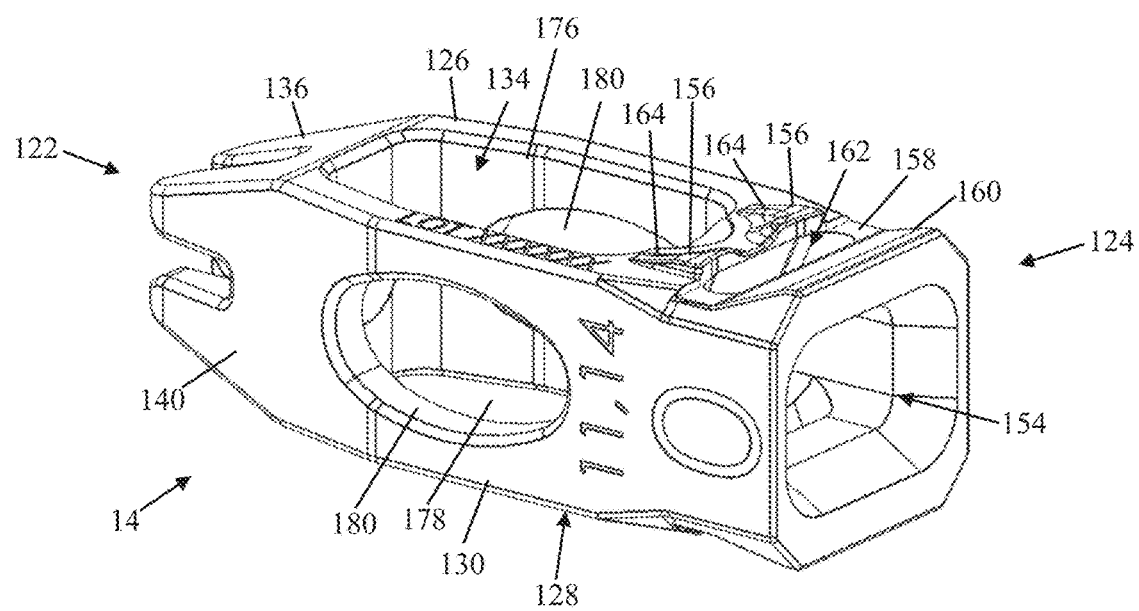
Figure 10:
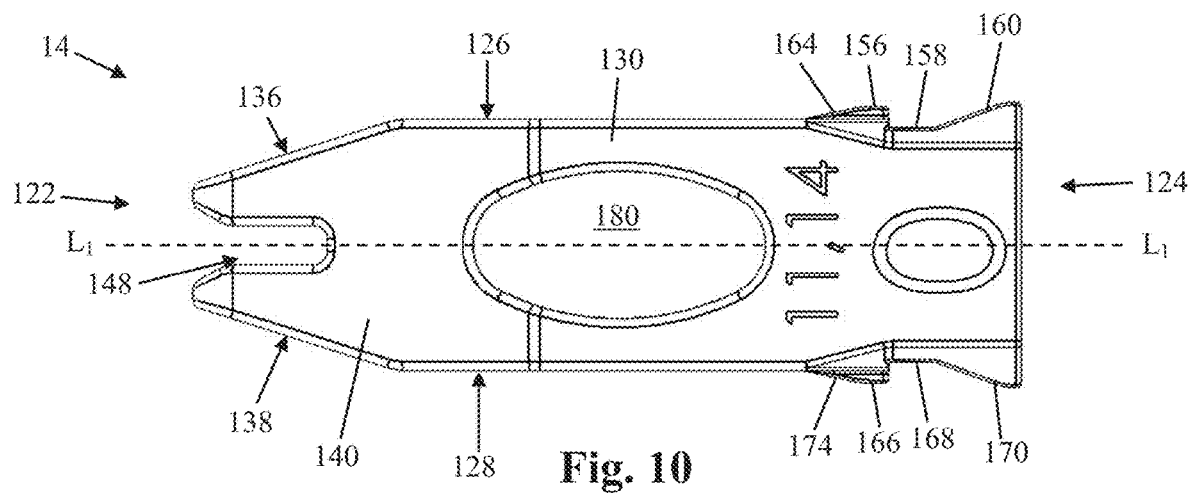
FIGS. 10-12 are various plan views of the surgical implant of FIG. 1.
Figure 11:
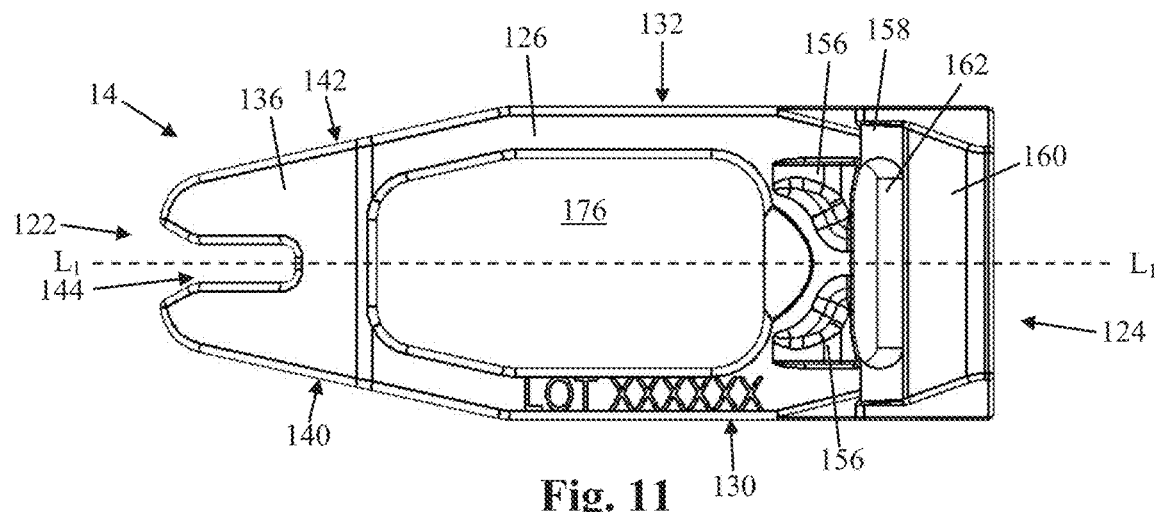
Figure 12:
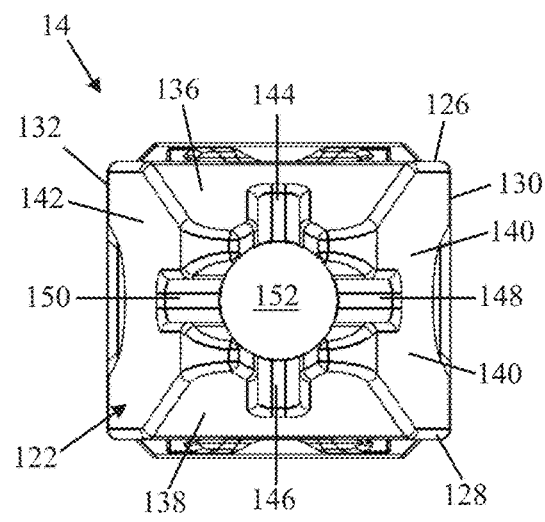
Figure 13:
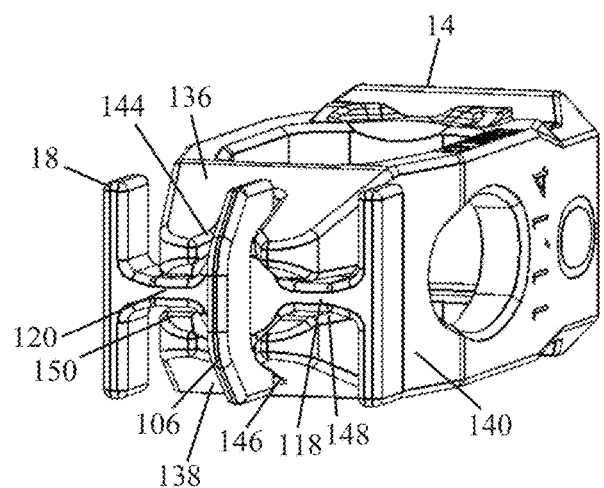
FIG. 13 is a perspective view of the shim of FIG. 8 coupled with a guide element of FIG. 5.

FIGS. 5-7 illustrate the guide element 18 in further detail. By way of example, the guide element 18 according to the present example may be made from any suitable medical grade material, including but not limited to metal alloys (e.g. cobalt chromium), titanium alloys (e.g. Ti6Al4V, nickel titanium), or polymers (e.g. PEEK, polyetherimide (Ultem), polyimide, polyamide). The guide element 18 of the instant example includes a base 96, a leading side 98, and a trailing side 100. The base includes a post 102 extending perpendicularly from the trailing side, the post 102 being configured to engage an instrument such as an inserter. By way of example, the post 102 includes threads 104 for threaded engagement, however other engagement mechanisms are possible, for example snap-fit, ratchet, and the like. The central flange 106 extends perpendicularly from the leading side 98 of the base 106, has a height dimension that is substantially identical to the height dimension of the shell 16, and at least a partial perimeter shape that coincides with the shape of the leading end 24 of the shell 16. More specifically, the central flange 106 has a leading edge 108 including first and second tapered portions 110, 112 that align with the tapered portions of the smooth outer leading surfaces of the distal panels 64, 66, 68, 70, so that when the implant is in the initial, collapsed state, the central flange 106 and distal panels 64, 66, 68, 70 present a smooth, closed leading surface to facilitate advancement of the implant 10 into the target disc space.

The guide element 18 further includes first and second lateral flanges 114, 116 connected to the base 96 by way of first and second transverse connectors 118, 120. Each of the first and second lateral flanges 114, 116 has a generally rectangular perimeter shape (for example, however other shapes are possible) and a height dimension identical to the height dimension of the central flange 106. The distance between the central flange 106 and either of the first and second lateral flanges 114, 116 determines the maximum distance that the shell 16 is able to expand laterally during shim insertion, as they provide a physical barrier for the first, second, third, and fourth extension arms 72, 74, 76, 78, respectively.

In some embodiments, the guide element 18 is not attached to the shell 16 but is held in place by different elements during different stages of the insertion process. For example, prior to insertion, the guide element 18 can be held in place by the distal panels 64, 66, 68, 70 of the collapsed implant (e.g. FIG. 1). During insertion (and more specifically during shim 14 insertion) the guide element 18 can be held in place due to its connection to the inserter (not shown). Finally, after insertion the guide element 18 can be held in place by the leading end 122 of the shim 14 (e.g. FIG. 13).

FIGS. 8-13 illustrate one example of a shim 14 in further detail. The shim 14 drives the expansion of the shell 16 upon insertion of the shim 14 through the aperture 80 and into the central lumen 92. The degree of shell 16 expansion in any direction is directly correlated to the size and shape of the shim 14. Therefore, the shim may be provided in various sizes and shapes without departing from the scope of the disclosure. By way of example, the shim 14 includes a leading end 122, trailing end 124, top 126, bottom 128, a first side 130, a second side 132, and a central lumen 134.

The leading end 122 can be configured to be introduced into the aperture 80 at the trailing end 26 of the shell 16 and thereafter cause expansion of the shell 16 as the shim 14 continues advancement into the central lumen 92. To facilitate this, each of the top 126, bottom 128, first side 130, and second side 132 can include a tapered surface 136, 138, 140, 142, respectively, that tapers distally toward the central longitudinal axis $L_1$ of the implant 10. The slope of the individual tapered surfaces determines how quickly the shell 16 expands to maximum height/width, and may be different for the different surfaces. Each tapered surface 136, 138, 140, 142 has a slot 144, 146, 148, 150 formed therein that is configured to receive a portion of the guide element 18 during coupling of the shim 14 and shell 16 (see e.g. FIG. 13). More specifically, the tapered surface 136 can have a slot 144 configured to receive a first portion of the central flange 106, the tapered surface 138 can have a slot 146 configured to receive a second portion of the central flange 106, the tapered surface 140 can have a slot 148 configured to receive at least a portion of the first transverse connector 118, and the tapered surface 142 can have a slot 150 configured to receive at least a portion of the second transverse connector 120. The leading end 122 can further include an aperture 152 sized and configured to enable passage of the post 102 of the guide element 18 through the leading end 122 and into the central lumen 92 so that the post 102 is accessible for coupling with an insertion instrument (not shown) by way of aperture 80 and central lumen 92.

In some embodiments, the trailing end 124 includes an axial aperture 154 sized and configured to allow passage of one or more instruments (e.g. inserter, graft applicator, etc) through the trailing end 124 and into the central lumen 134. The top surface 126 at the trailing end 124 includes one or more locking barbs 156, a transverse recess 158 positioned posterior of the one or more locking barbs 156, a posterior ramp 160 positioned posterior of the transverse recess 158, and an engagement aperture 162 formed within the recess 158 for engaging with a surgical instrument such as a shim removal tool. Each locking barb 156 includes a ramped surface 164 ascending posteriorly to the edge of the recess 158. The one or more locking barbs 156 and transverse recess 158 interact with the first and second medial flanges 82, 84 of the shell 16 to securely hold the shim 14 within the shell 16 after the shim 14 has been fully inserted. More specifically, as the trailing end 124 of the shim 14 passes into the central lumen 134, the first and second medial flanges 82, 84 will slideably engage the ramped surface(s) 164 of the locking barb(s) 156 and be displaced slightly as the locking barb(s) 156 pass by, at which point the medial flanges 82, 84 will snap back into place within the transverse recess 158. This action not only produces an audible and tactile "click", but also places the medial flanges 82, 84 in position to prevent unwanted posterior migration of the shim 14 after the surgery has been completed. The surgeon may confirm that the shim 14 has been fully inserted by viewing the construct under fluoroscopy and ensuring that the locking barb(s) 156 are anterior of the two radiographic markers 44 positioned at the trailing end 26 of the shell 16 (see, e.g. FIGS. 12-13).

In some embodiments, the bottom surface 128 at the trailing end 124 can be essentially a mirror image of the top surface 126 at the trailing end 124, and includes one or more locking barbs 166, a transverse recess 168 positioned posterior of the one or more locking barbs 166, a posterior ramp 170 positioned posterior of the transverse recess 168, and an engagement aperture 172 formed within the recess 170 for engaging with a surgical instrument such as a shim removal tool. Each locking barb 166 includes a ramped surface 168 ascending posteriorly to the edge of the recess 168. The one or more locking barbs 166 and transverse recess 168 interact with the third and fourth medial flanges 86, 88 of the shell 16 to securely hold the shim 14 within the shell 16 after the shim 14 has been fully inserted. More specifically, as the trailing end 124 of the shim 14 passes into the central lumen 134, the third and fourth medial flanges 86, 88 will slideably engage the ramped surface(s) 174 of the locking barb(s) 166 and be displaced slightly as the locking barb(s) 166 pass by, at which point the medial flanges 86, 88 will snap back into place within the transverse recess 168. This action not only produces an audible and tactile "click", but also places the medial flanges 86, 88 in position to prevent unwanted posterior migration of the shim 14 after the surgery has been completed. The surgeon may confirm that the shim 14 has been fully inserted by viewing the construct under fluoroscopy and ensuring that the locking barb(s) 166 are anterior of the two radiographic markers 44 positioned at the trailing end 26 of the shell 16.

The first and second sides 130, 132 are smooth at the trailing end 124. The shim 14 further includes large top and bottom graft windows 176, 178 formed in the top and bottom surfaces 126, 128, respectively, and side graft windows 180 formed in the first and second sides 130, 132. The graft windows allow for the use of bone graft material (e.g. biologic bone, artificial bone matrix, collagen, protein, etc.)

It should be appreciated that, although the shim illustrated in FIGS. 8-13 is not "asymmetrical", it can be in some embodiments. As can be appreciated, in some embodiments, the system can be designed such that the asymmetry of the shell is configured to extend out in the intervertebral space in a direction that is away from, or perhaps opposite, the location of the shell due to the entry profile. In some embodiments, an anterolateral approach results in an anterior location, or anchor point, of the shell upon entry, so the asymmetry can be configured to extend away from the anterior location, reaching to the medial region of the intervertebral space. In some embodiments, a posterolateral approach results in a lateral location of the shell upon entry, or anchor point, such that the asymmetry can be configured to extend away from the lateral location, reaching to the medial region of the intervertebral space. In some embodiments, if the anchor point of the shell is central, or medial, in the intervertebral space, and the asymmetry can be configured to extend away from the medial location in any direction, either anterior, posterior or lateral in the intervertebral space. In some embodiments, the shim can be configured to include a biased extension or asymmetry, for example, to take further advantage of providing support to the asymmetric extension of the shell from the entry location, or anchor point.

Figure 14A:
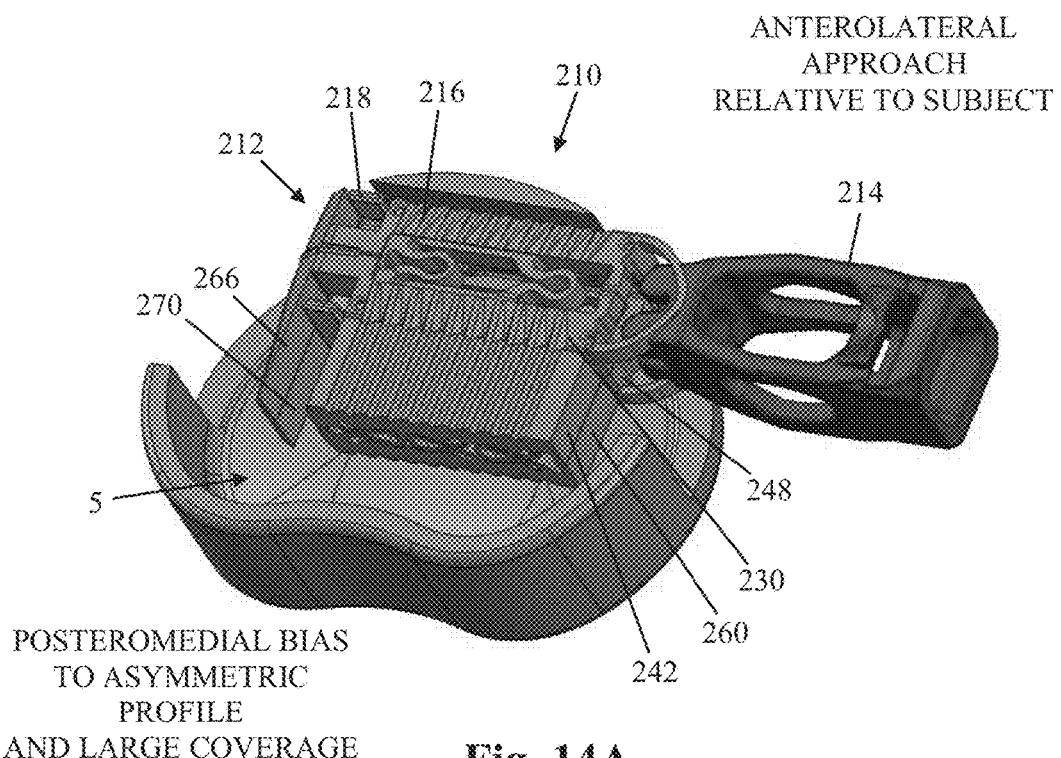
FIGS. 14A and 14B provide a perspective view of another example of a surgical implant delivered using an anterolateral approach, according to an embodiment, FIG. 14A showing a collapsed shell assembly inserted within a prepared intervertebral disc space, prior to insertion of the shim and FIG. 14B showing the shim fully expanded in the shell.
Figure 14B:
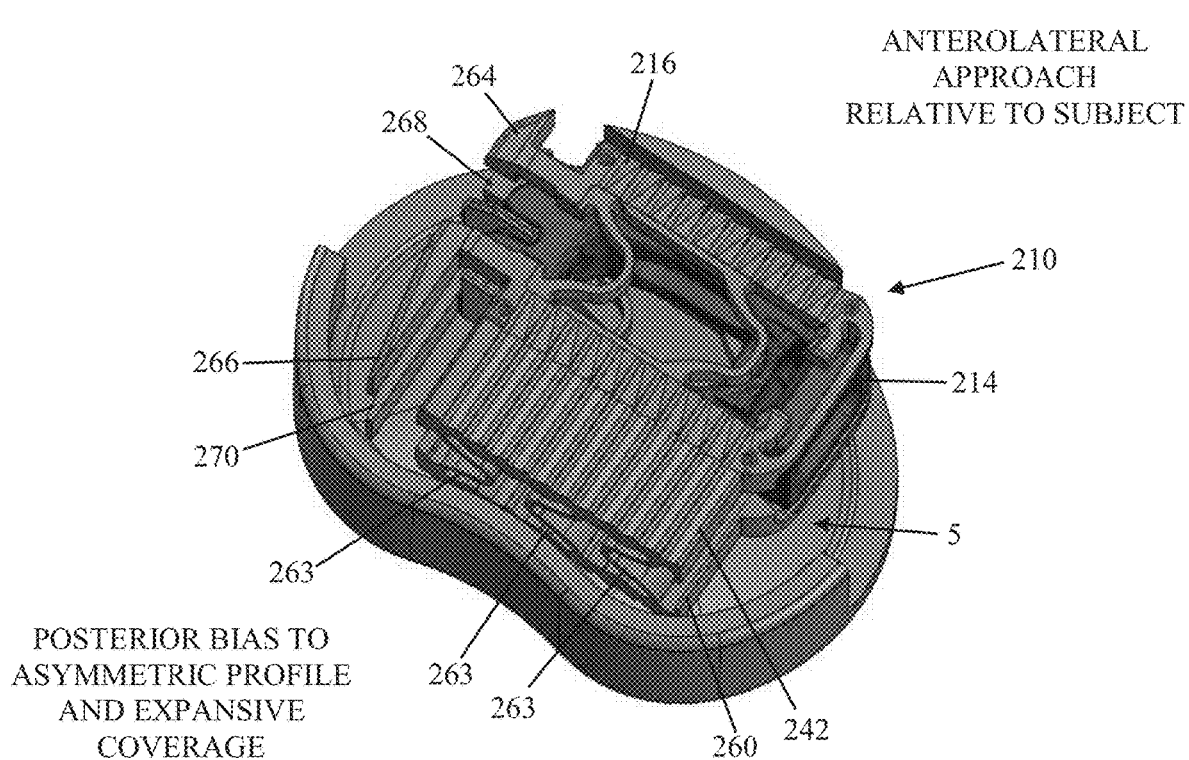

FIGS. 14A and 14B illustrate an anterolateral approach to implanting the device, oriented relative to the subject, according to an embodiment. A transverse section of an intervertebral space having a surgical implant 210 is shown. It should be appreciated that the surgical implant 210, however, is configured for use in either a posterolateral or anterolateral approach. FIG. 14A illustrates a collapsed shell assembly 212 inserted within a prepared intervertebral disc space 5, prior to insertion of the shim 214, while FIG. 14B illustrates an expanded shell assembly 212 within the disc space 5 with the shim 214 fully inserted. Interestingly, FIG. 14A shows the process starting with a posteromedial bias in the collapsed state, already showing large coverage, and FIG. 14B shows a more posterior bias with expansive coverage in the expanded state. The shell assembly 212 includes a shell 216 and a guide element 218. It should be understood that the surgical implant 210 of the present example can be compared to the surgical implant 10 disclosed above with a few notable exceptions that will be described in detail below. For example, the shim 214 of the instant example can be compared to the shim 14 described above and the guide element 218 of the present example can be compared to the guide element 18 described above. As such, repeated disclosure of identical elements is avoided with the understanding that, generally speaking, an element or feature described in conjunction with a particular example embodiment may be applied to other example embodiments without departing from the scope of the disclosure.

Figure 15:
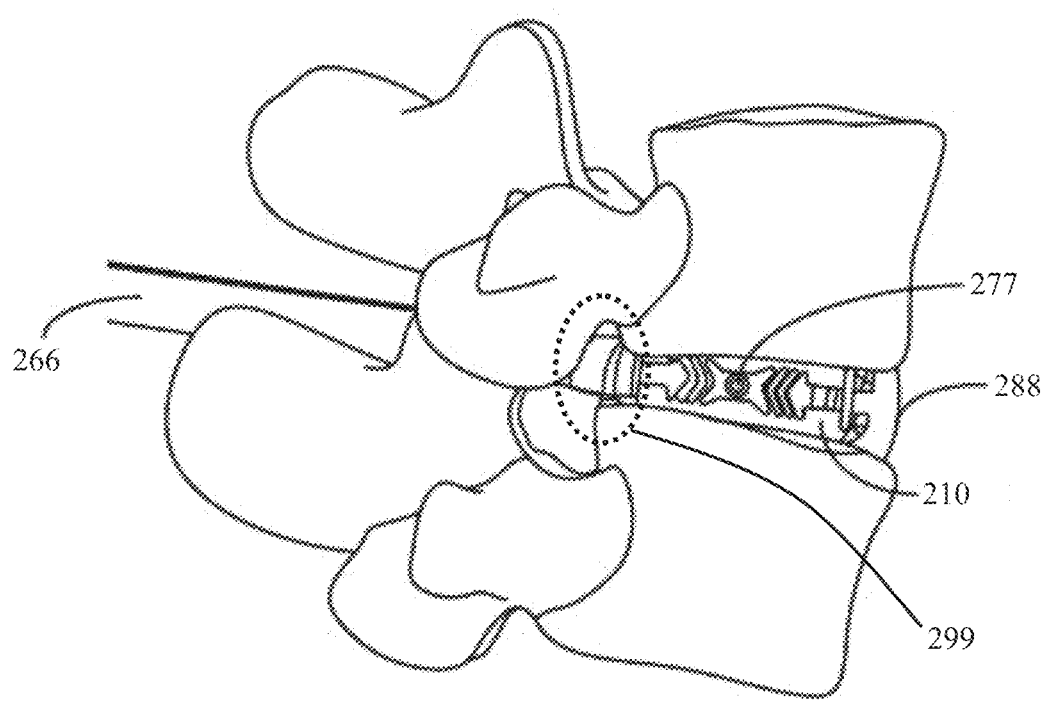
FIG. 15 shows how the device provides a clinical safety advantage by avoiding a need to maneuver around tissue in the region of the annulotomy to position the implant, according to an embodiment of the invention.
Figure 16:
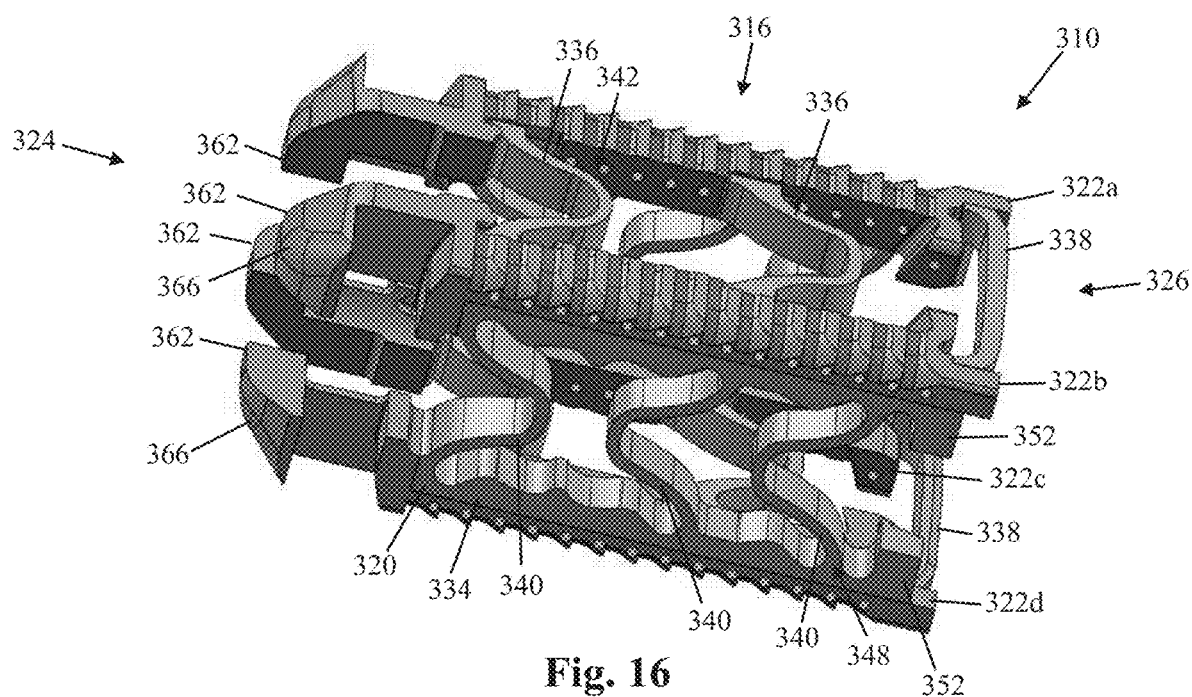
FIGS. 16-17 are perspective views of a shell assembly forming part of another example of a surgical implant, according to an embodiment.
Figure 17:
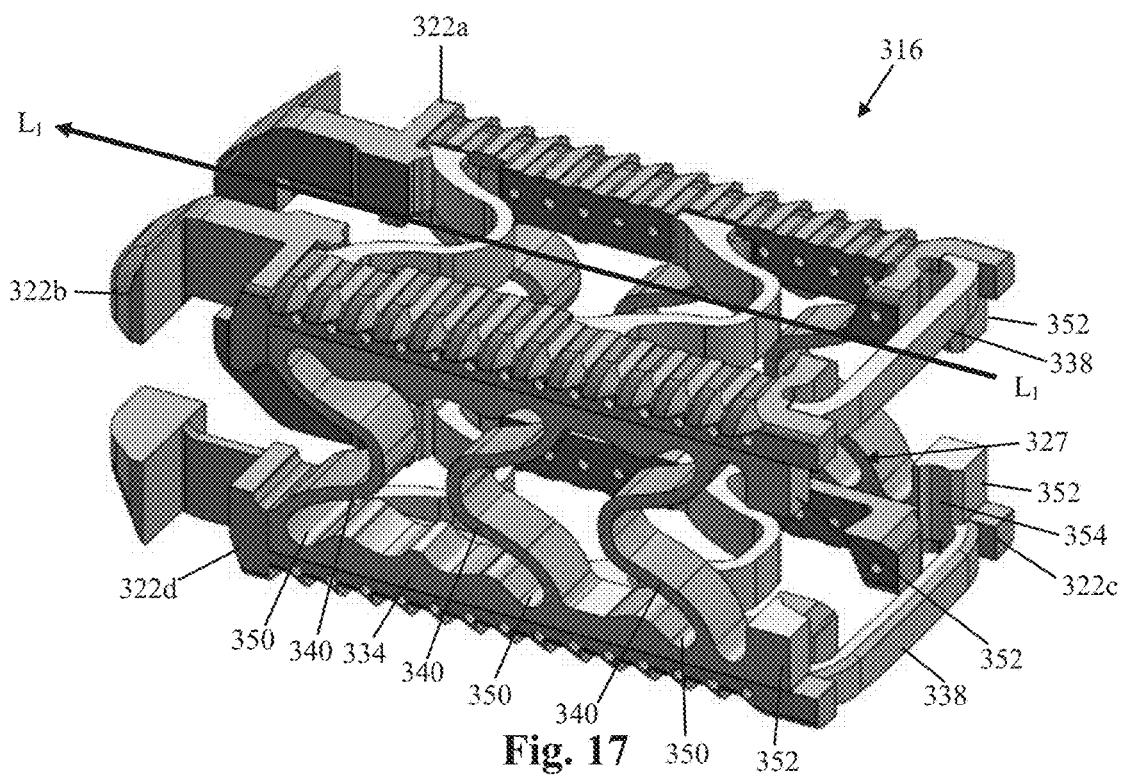
Figure 18:
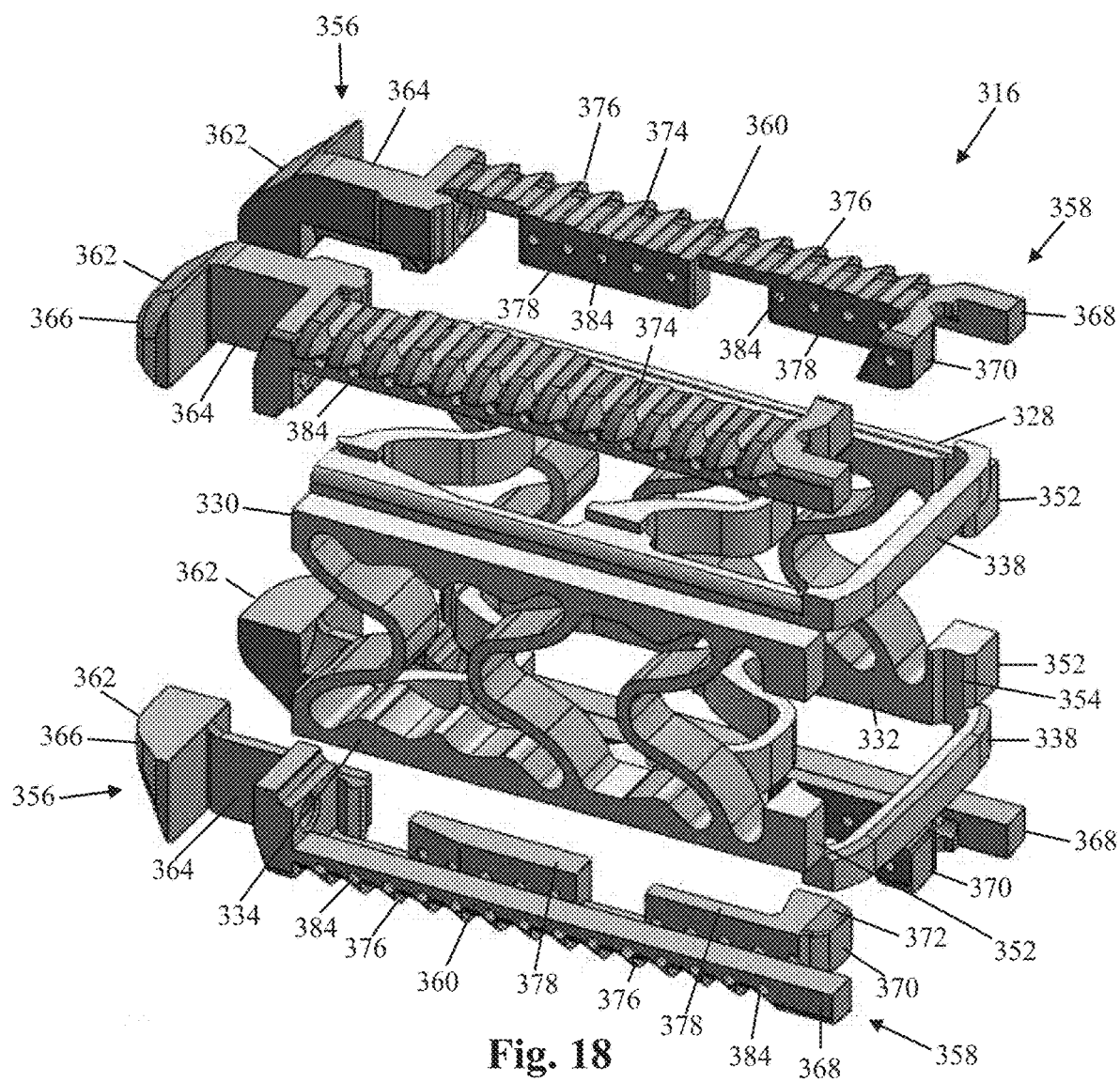
FIG. 18 is an exploded perspective view of the shell assembly of FIG. 16, according to an embodiment; and, FIG. 19 is a perspective view of the shell assembly of FIG. 16 prior to coupling with a shim element, according to an embodiment.
Figure 19:
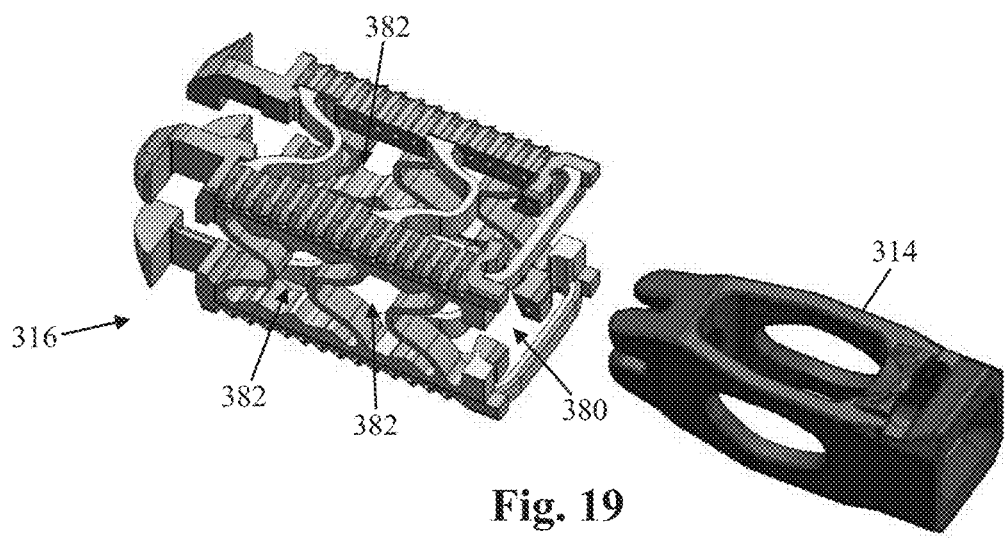

FIG. 15 shows how the device provides a clinical safety advantage by avoiding a need to maneuver around nerves in the region of the annulotomy to position the implant, according to an embodiment of the invention. FIG. 14A illustrates how the shim 214, and instrument that inserts the shim into the shell (not shown), are initially positioned asymmetrical to the disc during the implantation procedure, and are also inserted into the disc in an asymmetrical position at the onset of expansion. The problem with other fusion devices is that the positioning of such a device as desired in the intervertebral space can require substantial maneuvering to reposition the implant through the location of the annulotomy, and this can make it difficult-to-impossible to avoid an undesirable contact with surrounding tissue, such as nerve tissue, in the region of the annulotomy. As shown in FIGS. 14A and 14B, however, the expanding asymmetrical implants taught herein address the problem. FIG. 14A shows an initial positioning of the collapsed shell before insertion of the shim, the collapsed shell already reaching in the direction of the desired medial location, and FIG. 14B shows how the positioning of the shell has not changed and the expansion extended the implant further to the medial region of the intervertebral space. As such, the implant remained in its initial location without further maneuvering, and a desired positioning of the implant was reached through expansion alone, without having to otherwise reposition instruments during implantation which can disturb and damage surrounding tissue. As can be seen, the asymmetric shims and methods taught herein allow the shim to be inserted to expand the shell, and the shell expanded, while the transverse width and position of elements outside the disc (shim and expansion instrument) remain fixed while the shell is expanding. FIG. 15 illustrates how there is an improved nerve safety in a posterolateral approach, where shim 277 has been inserted to asymmetric shell 210 using expansion instrument 266 through a region 299 that includes an annulotomy and nerve tissue in the region 299 which is undesirably close to the annulotomy and subject to risk of damage. Using the asymmetric implants and methods taught herein, however, the transverse width and position of elements outside the disc (shim and expansion instrument) remain fixed while the shell is expanding, allowing the implant to expand into the desired location in the intervertebral space without repositioning the expansion instrument and risking undue contact with the nerve tissue in the region of the annulotomy. One of skill will appreciate that the asymmetric implants and methods taught herein provide a great clinical safety advantage, as there are currently no implants on the market that can expand horizontally and vertically while maintaining good strength and stability long-term while avoiding instrument shifting during expansion that may impinge on sensitive anatomy like nerve tissue.

The primary difference in surgical implant 210 as compared with the previously described surgical implant 10 lies in its size. Because the surgical implant 210 is configured for use with a lateral or anterolateral approach, a wider shell 216 may be used. Typically, the access is more anterior to avoid impinging on the psoas plexus nerves. This access direction also allows for greater access to the disc space 5. As a result, the implant 210 includes second and fourth elongated support beams 230, 248 having extra-wide lateral extensions 242, 260 so that, when the shim 214 is inserted to expand the shell 216, the shell expands asymmetrically with the greater expansion in the posterior direction. During shell expansion, the shim and insertion instrument will not migrate, or position themselves themselves in the process, posteriorly, greatly reducing the risk of impinging upon surrounding nerve tissue such as the psoas plexus. In the instant example, the second and fourth distal panels 266, 270 also have an increased width dimension.

FIGS. 16-19 illustrate an example of a surgical implant 310 according to another embodiment. By way of example, the surgical implant 310 of the present disclosure is a spinal fusion implant that may be inserted into an intervertebral disc space during a minimally invasive or open spinal fusion surgery. After insertion into the disc space, the surgical implant 310 of the present disclosure is expandable in multiple directions to create an improved footprint within the disc space, which in turn enhances the stability of the fusion surgery. Multiple graft windows allow for the use of bone graft material (e.g. biologic bone, artificial bone matrix, collagen, protein, etc.). By way of example, the surgical implant 310 of the present disclosure includes a multi-axially expandable, unibody structure having a generally rectangular cross-sectional shape and a central longitudinal axis $L_1$ parallel to a long edge of the implant 310, and has surface layers made of stronger material than the central layer, which has flexion elements. The surgical implant 310 of the present example includes a shell assembly 312 that is inserted into a surgically prepared target disc space and a shim 314 that is thereafter inserted into the shell assembly 312 to facilitate expansion of the shell assembly 312 within the target disc space. When fully inserted into the shell assembly 312, the shim 314 securely couples with the shell assembly 312 to provide stability to the expanded construct.

By way of example, the shell assembly 312 includes a shell 316 and a guide element 318 (not shown). The shell 316 includes a central layer 320, a plurality of surface layers 322a-322d, leading (or "distal") end 324, a trailing (or "proximal") end 326, and a central lumen 327 extending therethrough. When the surgical implant 310 has been implanted within an intervertebral disc space, the top pair of surface layers 322a, 322b will contact an endplate of a first vertebral body and the bottom pair of surface layers 322c, 322d will contact an endplate of a second vertebral body. The central lumen 327 extends through the shell 316 and is sized and configured to allow passage of any instrument used during insertion, including but not limited to an inserter, various cannula and the like, as well as graft material (e.g. biologic bone, synthetic bone matrix, collagen, protein, etc.) and the shim 314.

The central layer 320 includes first, second, third, and fourth elongated support beams 328, 330, 332, 334, each comprising a long edge of the generally rectangular box-like shape of the implant, and each support beam extending parallel to the longitudinal axis $L_1$. The central layer 320 further comprises a plurality of transverse flexion struts 336, proximal flexion struts 338, and vertical flexion struts 340 extending between and connecting the various support beams to one another. The example shown by way of illustration includes a first pair of transverse flexion struts 336 positioned directly between the first and second support beams 328, 330, defining a top face 342 of the central layer 320. A second pair of transverse flexion struts 336 positioned directly between the third and fourth support beams 332, 334 defines a bottom face 344 of the central layer 320. A first proximal flexion strut 338 connecting the first and second support beams 328, 330 is positioned at the trailing end 326, and a second proximal flexion strut 338 connecting the third and fourth support beams 332, 334 is also positioned at the trailing end 326. A first plurality of vertical flexion struts 340 (for example, three) is positioned between the first and third support beams 328, 332, defining a first lateral face 346 of the shell 316. A second plurality of vertical flexion struts 340 is positioned between the second and fourth beams 330, defining a second lateral face 348 of the shell 316. The number and configuration of the various flexion struts is shown and described by way of example only, however any number of flexion struts may be used without departing from the scope of this disclosure.

When the implant 310 is in a compressed position, each of the various flexion struts (transverse, proximal, and vertical) has a length dimension that is greater than the distance between the relevant support beams. As such, the transverse flexion struts 336 and vertical flexion struts 340 are bowed to fit between the corresponding support beams without breaking the plane of the support beams. The bowed flexion struts maintain a curved orientation at the apex of the bowed shape (as opposed to a sharp angle), which is located at the midpoint of the distance between the support beams, and preferably having a radius within the range of 0.005-0.5" (and more preferably 0.020-0.128") to prevent stress cracking. By way of example, the bowed shape may be generally "U"-shaped, "C"-shaped, "S"-shaped, "W"-shaped, or sinusoidal. The transverse flexion struts 336 are bowed in a proximal direction and are generally uniform in thickness in the proximal-distal direction however the strut thickness may be increased at either end of the struts near the junctions with support beams. The vertical flexion struts 340 may be bowed in a proximal or distal direction and have a uniform thickness in the proximal-distal direction. By way of example, the two proximal-most vertical flexion struts 340 in the first lateral face 346 and second lateral face 348 are bowed in a distal direction to facilitate insertion of the shim 314, since as the shim 314 is advanced into the central lumen 327, the lateral faces 346, 348 and thus the vertical struts 340 contained therein are pushed outward laterally ahead of the shim 314. By way of example, the strut thickness in the proximal-distal direction may be between 0.1-2 mm and preferably 0.2-1 mm. This amount of thickness allows for bending of the struts during collapsing or expansion of the shell 16 without excessive strain on the struts. The flexion struts may have a thickness in the range of 2-12 mm in the transverse direction (perpendicular to the proximal-distal axis). This increased thickness in the transverse direction is desired to maintain a high structural stiffness and strength in the transverse direction so that the transverse cross section shape is maintained during and after insertion into the disc space, during implant expansion when the shim 314 is inserted into the shell 316, and after the surgery when the patient resumes normal activity.

The aspect ratio of the longitudinal:transverse thickness of the struts can be configured to provide the desired amount of strength, stiffness, and ability of the implants to retain their shape under the forces they experience in the intervertebral space. It should also be appreciated that, in some embodiments, the maintaining of the structural integrity of the surgical implants is highly desired. In some embodiments, for example, the connectors, or struts, are designed to have an aspect ratio of longitudinal thickness to transverse thickness ranging from about 1:2 to about 1:16, from about 1:2 to about 1:12, from about 1:2 to about 1:10, from about 1:2 to about 1:8, or any range therein in some embodiments. Structural integrity can include, but is not limited to, at least inhibiting torsional movement of the first, second, third, or fourth support beam around its own central axis after expansion; deformation of the first, second, third, or fourth support beam around the shim; and, the like.

The central layer 320 further includes a plurality of "V" shaped slots 350 formed therethrough near the junction of each end of each strut and the corresponding support beams, starting at a distance of 1-4 mm (0.5-8) from each support beam corner to effectively render "V" shaped struts. The slots 350 may be formed perpendicular to the longitudinal axis $L_1$ or angled distally from the outside in. The distally angled formation renders struts that have distally angled surfaces on the side facing the central lumen 327 to facilitate insertion of the shim 314. The V-shaped slots 350 that form gaps between the vertical struts 340 narrow as the shell 316 is collapsed to keep the outer surfaces of the lateral faces 346, 348 smooth for insertion into the disc space. Additionally, the inner surfaces (e.g. facing the central lumen 327) of the lateral faces 346, 348 are smooth to facilitate insertion of the shim 314 into the central lumen 327. Once the shell 316 is expanded, the size of the gaps increase rendering surfaces that are rougher to help embed the implant 10 within the tissues in the disc (vertebra and annulus) and to hold the shim 314 in place to maximize implant stability. Furthermore the angle of contraction lies in a plane parallel to the longitudinal axis $L_1$ of the shell 316 so that it flexes in that plane and thus does not alter the sidewall thickness of the implant 10. This is desired to minimize the outer profile for insertion while maximizing the size of the central lumen 327 to allow the shim 314 to be inserted for expansion after the shell 316 has been inserted into the disc space. This geometry, combined with the solid beams on the corners ensure that the implant has minimal change in length (e.g. less than 15%) during significant lateral and/or vertical expansion (e.g. more than 20%). In fact, the surface layers 322*a*-322*d* that engage the vertebra are constant in length regardless of shell 316 expansion. This is desired to allow the surgeon to be precise about getting an implant 310 into the disc space that is the correct length unlike other technologies that expand by shortening the implant by the same amount. Furthermore this set of angled strut patterns on each side of the implant 310 allow for independent horizontal and vertical expansion. In other words the amount of horizontal expansion is independent of the amount of vertical expansion, and depends entirely upon the shim 314 used for expansion. This allows for a more controlled variety of aspect ratios so that the implant 310 can best fit the target disc space.

The proximal flexion struts 338 are attached at either end to the proximal ends of the support beams. As with the transverse and vertical flexion struts 336, 340, the proximal flexion struts 338 have a length that is greater than the distance between the various support beams. As such, the proximal flexion struts 338 are bowed in a proximal direction. The bowed flexion struts 338 maintain a curved orientation at the apex of the bowed shape to prevent stress cracking. By way of example, the bowed shape may be generally "U"-shaped, "C"-shaped, "S"-shaped, "W"-shaped, or sinusoidal. The proximal flexion strut 338 is generally uniform in thickness in the proximal-distal direction.

Each of the elongated support beams 328, 330, 332, 334 includes a corner post 352 located at the proximal ends of the support beams and extending perpendicularly toward the midline of the implant in the same direction as the vertical struts 340. The corner posts 352 provide additional stability and rigidity to the implant. The proximal faces of the corner posts 352 have inward, distally angled chamfers 354 to allow for initial insertion of the shim 314 that itself is tapered distally. Each of the elongated support beams 328, 330, 332, 334 further includes an elongated cutout region/shelf 355 extending the entire length of the corresponding support beam. Each shelf 355 provides an interface with the surface layers 322a-d.

The central layer 320 is preferably made from strong but ductile material such as polymers with tensile modulus of around 200-600,000 psi and tensile strength of around >9000 psi, and ability to strain more than 4% to break and preferably more than 20% to break. The ability to achieve high strain to break is essential for the various flexion struts to flex enough to allow the shell 316 to expand in a least 2-3 directions (vertical, horizontal and angles). In the current example embodiment, the shell 16 is made from polyetheretherketone (PEEK), however any suitable medical grade material may be used to manufacture the shell 316, including but not limited to polymers (e.g. PEEK, polyetherimide (Ultem), polyimide, polyamide), metal alloys (e.g. cobalt chromium), or titanium alloys (e.g. Ti6Al4V, nickel titanium). If metal is used to make the central layer 320, then strut thickness may be reduced by 3-5 times in the long axis direction.

By way of example, the surface layers 322a-d are either identical or mirror images of each other and all have the same features. Thus, any feature described in relation to one of the surface layers may be applicable all surface layers. Each of the surface layers 322a-d includes a leading end 356, trailing end 358, and an elongated beam 360 extending between the leading and trailing ends 356, 358.

In the current example, the leading end 356 of each of the surface layers 322a-322d comprises a distal panel 362 that, while the implant 310 is in an initial, collapsed state (e.g. as it would be during the insertion process), is arranged with the distal panels 362 of the other surface layers in such close proximity to one another so as to create a solid wall at the leading end 356. Each of the four distal panels 362 has a generally rectangular perimeter and is arranged perpendicular to the longitudinal axis $L_1$. Each of the four panels 362 is integrally formed with an extension arm 364 that extends distally from a distal end of one of the aforementioned elongated beams 360. Each distal panel 362 includes a smooth outer leading surface 366 that is at least partially tapered to provide for easier insertion into the disc space. As with the implant 10 described above, when the implant 310 is in the initial, collapsed state, the distal panels 362 align with the central flange of the guide element (not shown) to form a "closed" surface at the leading end 324 of the implant 310 to prevent seepage of body fluids and/or tissue into the implant during insertion into the target disc space.

The trailing end 358 of each of the surface layers 322a-322d includes a longitudinal flange 368 and a medial flange 370. The longitudinal flanges 368 extend proximally from the proximal end of the elongated beam 360 in a direction parallel to the longitudinal axis $L_1$ and provide support and stability to the assembled (or machined) construct. The medial flanges 370 each extend perpendicularly inward from the proximal end of the respective elongated beam 360 such that, while the implant 310 is in an initial, collapsed state (e.g. as it would be during the insertion process), the medial flanges 370 are arranged in such close proximity to one another so as to create a rigid crossbar at the trailing end 326 of the shell 316 to increase implant stability. Each of the medial flanges 370 is integrally formed with one of the aforementioned elongated support beams 360. The medial flanges 370 each include a proximal-facing smooth tapered surface 372 to provide for easier insertion of the shim 314 into the shell 316.

The elongated beam 360 includes an outer surface 374 adapted to interface with the body tissue (e.g. vertebral endplate). The outer surface 374 may include any number of anti-migration features 376 to ensure the implant 310 remains in place after insertion into the patient's intervertebral disc space. By way of example, the anti-migration features 376 may include a plurality of teeth (as shown in FIGS. 16-19), spikes, surface roughening, friction elements, and the like. Additionally, there are ledges 378 protruding inwards from the corners that provide a strong track for the shim 314 to ride inside to push up to expand the shell 316 outward and maintain the expansion. The ledges 378 are part of the strong and stiff surface layer to achieve stability during and after expansion of the shell 316.

The trailing end 326 of the shell 316 includes an aperture 380 that provides access to the central lumen 327 of the shell 316 when the implant 310 is in a collapsed orientation, such as during insertion into the disc space. The aperture 380 is sized and configured to allow passage of any instrument used during insertion, including but not limited to an inserter, various cannula and the like, as well as graft material (e.g. biologic bone, synthetic bone matrix, collagen, protein, etc.) and the shim 314. As such, unlike the "closed" configuration of the leading end 324 discussed above, the trailing end 326 has an "open" configuration.

The shell 16 further includes a plurality of graft windows 382. For example, the inserter passes through the aperture 380 and central lumen 327 and couples with the threaded post of the guide element (not shown) in the manner described above with respect to the implant 10. The graft windows 382 are relatively large and enable fusion of the graft material with tissue. There are graft windows 382 in the top and bottom faces 342, 344 of the implant 310 that are especially designed to accommodate flexion of the struts into when the shell 316 is collapsed but opens up larger as the shell 316 is expanded horizontally.

The surface layers 322a-322d are preferably highly osteogenic due to having a rough texture or being made of osteoconductive material such as roughened or porous metal (e.g. Titanium alloys, cobalt chromium or stainless steel). The surface layers 322a-322d may also be made of a ceramic (e.g. silicon nitride), hydroxyapatite, and/or any combination composite thereof. The layer may be porous throughout like bone or it may be dense in the base and roughened on the surface. The surface layers 322a-322d may have holes 384 for the polymer from the central lumen 327 to flow into to lock the surface layers 322a-322d into position.

In one embodiment of manufacturing the surgical implant 310, the central layer 320 and surface layers 322a-322d may be overmolded together. In such embodiment, the surface layers 322a-322d may be sintered/3D printed, molded or machined separately and then placed into a mold for the assembly where the polymer will flow into the mold to fill the central layer 320 and bind to surface layers 322*a*-322*d*. The surface layers 322*a*-322*d* may have holes 384, porous surfaces and/or undercuts to allow for mechanical locking due to polymer flowing into such features during the molding process. Alternatively, the central layer 320 may be molded or machined. The surface layers 322*a*-322*d* may be machined, molded or sintered. Then the layers are assembled by pressure, heat melting, snap fits, use of adhesive or a combination thereof.

The shim 314 is substantially the same as the shim 14 described above. The shim 314 functions to expand the surgical implant 310 after the shell 316 is inserted in the disc space, and to help to stabilize the shell 316 in the expanded state against in vivo forces. Once fully inserted, the width of the shim 314 is combined with the thicknesses of the side walls of the shell 316 to increase the width and height of the surgical implant 310 to be larger than the width and height of either the shell 316 or the shim 314 alone.

The multiaxially expandable, unibody structure of the surgical implant 310 of the present example enables highly repeatable and cost effective fabrication methods such as molding or other high speed automated fabrication methods. Only a small number of molds (1-2) are required to achieve implant with 4-20 times aspect ratios. The surface layer is optimized for strength, radiopacity and osteogencity/osteoconductivity without compromising the structural stiffness, expandability and central radiolucency by combining these layers of different materials. For example, the surface layers can be roughened metal (highly osteogenic/osteoconductive, radioopaque, very high strength) while the central layer is a polymer with bone-like modulus. The polymer is substantially less stiff than the metal. The layers stacked in series represents a "springs in series" model in which case the least-stiff element dominates the stiffness of the structure and renders it more like bone in stiffness which is favorable for stable bone healing (no stress shielding). The high strength of the surface layer allows the surgeon to mallet the cage into a tight disc without risking damage. The surface layers can help the cage maintain its shape better due to higher modulus strength than polymer for example. The radioopacity helps the surgeon to visualize the extent of the expansion and shape of the implant on X-Ray without compromising the ability to visualize bony fusion through the central portion of the cage long term.

In some embodiments, a shim can also be configured with a lateral bias to asymmetrically expand the shell to a biased footprint, or profile, in an intervertebral space. In some embodiments, the first body portion of the shell can have a first track beam that serves as a track by which the position of the shim is fixed relative to the shell, with regard to lateral movement in the shell, as the shim is inserted into the shell in a proximal-to-distal direction in vivo, such that a lateral bias of the shim becomes a lateral bias in the shell upon expansion. In some embodiments, the second body portion of the shell can, likewise, have a second track beam to fix the position of the shim relative to the shell, again with regard to the lateral movement in the shell. The track, in some embodiments, can be be a tongue-and-groove configuration that allows proximal-to-distal translation of the shim in the shell, or it can be a track-and-key configuration, or the like, wherein any translatable indicator configuration known to one of skill can be used to facilitate the bias of the shim creating an asymmetry or bias in the profile or footprint of the surgical implant in the intervertebral space.

We claim:

1. A surgical implant configured for placement within an intervertebral space, comprising:
   a laterovertically-expanding shell, the shell having a distal region and configured to create an intervertebral scaffolding system in vivo, the shell having a first body portion configured to engage a first vertebral endplate and a second body portion configured to engage a second vertebral endplate, the shell further including a collapsed state and an expanded state;
   a guide element that slidably engages with the distal region of the shell, the guide element having a first lateral flange, a second lateral flange, and a distance between the first lateral flange and the second lateral flange, wherein the distance between the first lateral flange and the second lateral flange is configured for retaining the shell from lateral movement that exceeds the expanded state; and,
   a shim having a longitudinal axis and configured for in vivo introduction into the shell when the shell is in a collapsed state and thereafter causing expansion of the shell to an expanded state, the expansion occurring in a first lateral direction, a second lateral direction, and a vertical direction to create a profile in the intervertebral space;
   wherein the shell is configured to extend asymmetrically from the longitudinal axis of the shim, extending further in the first lateral direction than in the second lateral direction to bias the profile of the implant in the first lateral direction after the expansion.

2. The surgical implant of claim 1, wherein the first body portion includes a first elongated support beam extending parallel to a first longitudinal axis of the shell, a second elongated support beam laterally displaced from the first elongated support beam and extending parallel to the longitudinal axis, and a plurality of connectors extending between and the first and second elongated support beams.

3. The surgical implant of claim 2, wherein the second body portion includes a third elongated support beam extending parallel to a second longitudinal axis of the shell, a fourth elongated support beam laterally displaced from the third elongated support beam and extending parallel to the longitudinal axis, and a plurality of connectors extending between the third and fourth elongated support beams.

4. The surgical implant of claim 3, wherein each of the first and second support beams has a length and an edge, and one of the first and second support beams includes a first lateral extension element extending in a direction away from the other of the first and second support beams, the first lateral extension element having a length dimension extending at least substantially the length of the respective support beam and a width dimension extending laterally away from the edge of the respective support beam.

5. The surgical implant of claim 4, wherein each of the third and fourth support beams has a length and an edge, and one of the third and fourth support beams includes a second lateral extension element extending in a direction away from the other of the third and fourth support beams, the second lateral extension element having a length dimension extending at least substantially the length of the respective support beam and a width dimension extending laterally away from the edge of the respective support beam.

6. The surgical implant of claim 5, wherein the first and second lateral extension elements extend in the same direction.

7. The surgical implant of claim 5, wherein the respective support beams having the first and second lateral extension elements each have a width dimension that is between 1.2 and 10 times greater than the width dimensions of the other respective support beams.

8. The surgical implant of claim 2, wherein the connectors are bowed in a proximal direction.

9. The surgical implant of claim 8, wherein the bowed connectors maintain a curved orientation at the apex of the bowed shape to prevent stress cracking.

10. The surgical implant of claim 1, wherein the shell is made from at least one of a polymer, metal alloy, and titanium alloy.

11. The surgical implant of claim 1, wherein the shell includes a central layer and a plurality of surface layers, the central layer and surface layers comprising different materials.

12. The surgical implant of claim 11, wherein the surface layers are made from at least one of titanium alloy, cobalt chromium, stainless steel, ceramic, silicon nitride, and hydroxyapatite.

13. The surgical implant of claim 11, wherein the central layer is made from a medical grade polymer.

14. The surgical implant of claim 13, wherein the medical grade polymer is one of PEEK, polyetherimide, polyimide, and polyamide.

15. A surgical implant having a combination of materials combined in layers, comprising:
 a laterovertically-expanding shell having a distal region and configured to create an intervertebral scaffolding system in vivo, the shell having a layered assembly that includes a central layer and a plurality of surface layers; wherein,
  the central layer has a top face and a bottom face, and is configured to associate with the plurality of surface layers;
  the plurality of surface layers has a top surface layer and a bottom surface layer, the top surface layer configured to associate with the top face of the central layer and form a first body portion configured to engage a first vertebral endplate; and the bottom surface layer configured to associate with the bottom face of the central layer and form a second body portion configured to engage a second vertebral endplate; and,
  the shell has a collapsed state and an expanded state;
 a guide element that slidably engages with the distal region of the shell, the guide element having a first lateral flange, a second lateral flange, and a distance between the first lateral flange and the second lateral flange, wherein the distance between the first lateral flange and the second lateral flange is configured for retaining the shell from lateral movement that exceeds the expanded state; and,
 a shim configured for in vivo introduction into the shell when the shell is in the collapsed state and thereafter causing expansion of the shell to the expanded state, the expansion occurring in a lateral direction and a vertical direction;
 wherein, the central layer and the plurality of surface layers comprise different materials.

16. The surgical implant of claim 15, wherein the central layer is made from a medical grade polymer.

17. The surgical implant of claim 16, wherein the medical grade polymer is one of PEEK, polyetherimide, polyimide, and polyamide.

18. The surgical implant of claim 15, wherein the surface layers are made from at least one of titanium alloy, cobalt chromium, stainless steel, ceramic, silicon nitride, and hydroxyapatite.

19. The surgical implant of claim 15, wherein the surface layers have at least one of a roughened and porous texture.

20. The surgical implant of claim 15, wherein the surfaced layers are associated with the central layer using at least one of pressure, heat melting, snap fit engagement, and adhesive.

* * * * *